(12) United States Patent
Petrenko

(10) Patent No.: US 7,405,508 B2
(45) Date of Patent: Jul. 29, 2008

(54) MICROMANIPULATOR

(76) Inventor: Serhiy Feclorovich Petrenko, ul. Kumatovskogo, d.6, kb. 26, Kiev 02139 (UA)

( * ) Notice: Subject to any disclaimer, the term of this patent is extended or adjusted under 35 U.S.C. 154(b) by 326 days.

(21) Appl. No.: 10/876,296

(22) Filed: Jun. 24, 2004

(65) Prior Publication Data
US 2005/0023930 A1    Feb. 3, 2005

(51) Int. Cl.
*H01L 41/08* (2006.01)
(52) U.S. Cl. .............. 310/317; 310/316.01; 310/323.02
(58) Field of Classification Search ............ 310/316.01, 310/316.02, 313, 323.02; 318/116–118
See application file for complete search history.

(56) References Cited

U.S. PATENT DOCUMENTS

| | | | | |
|---|---|---|---|---|
| 4,019,109 | A | | 4/1977 | McCoy et al. |
| 4,400,641 | A | * | 8/1983 | Vishnevsky et al. ..... 310/323.02 |
| 4,453,103 | A | * | 6/1984 | Vishnevsky et al. ..... 310/323.02 |
| 6,404,104 | B1 | * | 6/2002 | Maeno et al. .......... 310/323.02 |
| 6,736,361 | B2 | * | 5/2004 | Price ..................... 248/288.51 |
| 6,867,532 | B2 | * | 3/2005 | Brady et al. ........... 310/323.02 |
| 6,977,461 | B2 | * | 12/2005 | Hendriks et al. ............ 310/328 |
| 7,034,437 | B2 | * | 4/2006 | Fukagawa et al. ...... 310/316.03 |

OTHER PUBLICATIONS

World Precision Instrument, Catalogue, 1994.
Narishige Scientific Instrument (96.

* cited by examiner

*Primary Examiner*—Mark Budd
(74) *Attorney, Agent, or Firm*—I. Zborovsky

(57) ABSTRACT

The invention relates to precision instrument engineering and can be used in order to create microdisplacements in micron and submicron ranges for cellular microtechnologies (by engineering, gene engineering, reproductive diology and medicine, neurobiology, microphysiology, cytology, etc.), micromechanics and for the electronics and other industries. Said invention is characterized by reduced associated mechanical vibrations of a micromanipulator, high resolution (accuracy), a decreased number of single displacements, the extended speed adjustment range and functional capabilities of the micromanipulator. The inventive micromanipulator comprises a small movable table attached to a drive which is connected to a control unit and embodied in the form of a shaft provided with a rotor which is linked with annular piezoelements by means of pushers. One piezoelement is arranged on the shaft and the second piezoelement on a body. The control unit is embodied in the form of the following serially connected parts: a high-frequency pulse generator for piezoelement excitation, a controlled key, an amplifier connected to the corresponding piezoelement, a unit for generating the frequency of a pulse packet for piezoelement excitation and a unit for forming a burst time connected to the control input of the key.

39 Claims, 18 Drawing Sheets

MICROMANIPULATOR

The invention relates to precision instrument engineering and can be used in order to create microdisplacements in micron and submicron ranges for cellular micro technologies (bioengineering, gene engineering, reproductive biology and medicine, neurobiology, microphysiology, cytology, etc.), micromechanics, electronic and other industries.

Many micromanipulators MN-2, MN-3, MMN-1, MN-151, MN-15, etc. of the company "NARISHIGE" (Japan) are known. The basis of this micromanipulator is a movable table in linear guides and a manual drive which is connected through a screw-nut with the table. The manual micromanipulator until now is the simplest and most reliable, least expensive and widely spread micromanipulator. However, manual micromanipulators have a relatively low resolution ~10 ... 100 μm, which sharply reduces the area of their application.

Micromanipulators are known, which are based on a motorized microdisplacement of a movable table. This is a micromanipulator E of the company "LEITZ" (Germany), MM-88 of the company "NARISHIGE", etc. In these micromanipulators, the manual drive is replaced by a direct current motor, which provides high smoothness of its stroke, absence of vibrations, etc. However, these micromanipulators have a small resolution (~10 μm) and rather low dynamic characteristics make difficult free maneuvering in the image field of a microscope.

A motorized micromanipulator on stepper motors "DC3001" of the company "World Precision Instruments" USA is known (catalog 1994, page 47).

This micromanipulator includes a movable table connected through a screw-nut with a stepper motor, connected to a control block.

This micromanipulator operates in the following manner. By means of the control block, commands are formed to the stepper motor which carry out singular microdisplacements and also grouping of these microdisplacements is provided in time, which determines a speed of the microdisplacements.

The magnitude of the singular displacement (resolution) with this principle of micromanipulation and in this micromanipulator is determined by a step of the motor, and for the best stepper motors constitutes tens angular minutes. In the micromanipulator DC 3001 the magnitude of a minimal single microdisplacement is ~0.5 μm, which after recalculation to the angular step of the motor (with a transmission ratio of the micrometric screw-nut 1/300) is ~30 angular min. A further reduction of the microdisplacements in such systems can be achieved by providing of reducing transmissions for the motors, or by changing a transmission ratio fo the micrometric screw, which leads to complication of the construction, increase of sizes, labor consumption, and also to limitation of a possibility of time grouping of microdisplacements, that determines the speed of microfeed. Microdisplacements with such ideology of building of the system are directly tied to the speed, and vice versa.

The above mentioned disadvantages are eliminated in a micromanipulator disclosed in the patent of Russian Federation no. 2041480 "Micromanipulator" Int. Cl. G02B 21/32 which is selected as a prototype. This manipulator shown in FIG. 1, includes a movable table 1, located in bearing guides 2, connected with a micrometric screw-nut 3, adjoining through a movable coupling 4 a piezo-electric drive 5 formed as a shaft with a rotor 6 which is connected through pushers 9 with annular piezoelements 7 and 8, wherein one of them is arranged on the shaft and the second one is arranged on a housing, and a control system including a generator 10 of high frequency pulses for excitation of the piezoelements, a controlling key 11, formers 14, 13 of frequency and duration of packs of pulses of excitation of the piezo elements correspondingly and a power source 12.

This device operates in the following manner. By means of the formers 14, 13, a frequency and a duration of control signals is formed, which are supplied to the controlling key 11, and pulses of power supply are supplied from its output. A transformation of the feed pulses into packs of pulses of excitation at a resonance frequency of the piezoelement is performed in the generator 10. Under the action of these pulses, for example in the piezoelement 7, mechanical oscillations are formed. These oscillations are transmitted to the pushers 9, which are pushed from a lower piezoelement of the rotor which is frictionally-braked by the pushers, and form microdisplacements of the shaft. When the direction of rotation is changed, the piezoelement 8 is switched on. A torque imparted by the pushers of these piezoelement to the rotor 6 is transmitted through a frictional contact of the upper piezoelement and further to a load.

A step of the microdisplacement in this device is determined by the duration of the pack of pulses of excitation of the piezoelement, which is formed by means of the block 13, and a speed of the microdisplacement—by means of the block 14 which forms a frequency of proceeding of these packs.

This device allows to form an angular step at the level of tens angular seconds which after recalculation into standard screw-nut is equivalent to a linear displacement ~$10^{-2}$ μm (which already frequently is not enough), and also allows to realize a great range of regulation of speed, due to temporary grouping of the microdisplacements.

However, this high level of resolution of the system and broad range of regulation in accordance with speed is achieved on the account of a "rigid" start-stop characteristic of the piezoelectric drive in the control system (on the account of a fast acceleration and braking of the system). In other words, the more "rigid" the start-stop characteristic, the higher the level of resolution, but on the other hand also the higher the level of mechanical microfluctuations which accompany a singular step. This effect is increased when during the formation of the speed of displacement, a formation of singular steps into uninterrupted sequence of steps is provided. During this process the singular mechanical microfluctuations are transformed in a continuous vibration of the whole micromanipulator. The system of this class however must be "free" from vibrations, since insignificant vibrations on the micromanipulator can lead to significant levels of vibrations on the microobject (for example a micropipette), and these are micron and submicron ranges. In turn, this sharply reduces a real level of resolution (accuracy) of the system and a range of regulation in accordance with speeds.

The objective of the invention is: reduction of accompanying mechanical vibrations of a micromanipulator; increase of a resolution (accuracy); reduction of singular microdisplacements; expansion of a range of regulation in accordance with a speed; expansion of functional possibilities of the micromanipulator. This objective is solved in that, in a micromanipulator which includes a movable table connected with a drive, which is connected to a control block, with the drive formed as a shaft with a rotor connected through pushers with annular piezoelements, one of which is arranged on the shaft and the second one is arranged on the body, the control block includes connected in series, a generator of high frequency pulses of excitation of the piezoelement, a controlled key and an amplifier connected to a corresponding piezoelement.

In addition, it has, connected in series, a block for forming a frequency of packs of pulses of excitation of the piezoelement and a block of forming a duration of the pack of pulses of excitation, connected to the input of the control key.

A frequency of proceeding of the packs of pulses of excitation is more than 2 kHz, and a joystick is connected to a controlling input of each block of forming the duration of the pack of pulses of excitation of the piezoelement, wherein the duration of the pack of pulses of excitation and the output of the block of forming the duration is proportional to a "deviation", or to an logarithm of "deviation" of the joystick, while one of the outputs of the generator of the high frequency pulses of excitation of the piezoelement is connected to the input of the block of forming of a frequency of the packs of pulses of excitation of the piezoelement.

In addition, the control block is provided with a block of forming of a single pack of pulses of excitation of the piezoelement, connected to a controlling input of the key.

Annular piezoelements are formed as ring-shaped resonators with a radial shape of oscillations, and their outer cylindrical surface is embraced by a wave casing, on which pushers are arranged and abut against an inner surface of the rotor.

The annular piezoelements are polarized along a normal to their flat end surfaces, the electrodes are applied on the flat end surfaces, and their parameters satisfy the ratio $D/d\sim2$, $d/2\sim h$, wherein D is an external diameter of the annular piezoelement, d is an internal diameter of the annular piezoelement, h is a height of the annular piezoelement, and a frequency of the generator of high frequency pulses of excitation of the piezoelements corresponds to a zero mode of radial oscillations of the piezoelement.

The wave casing is formed as a thin-walled cylinder with fields folded out at both sides and forming ring-shaped reinforcing ribs, wherein the reinforcing ribs are cut by slots, in which pushers are fixed with their one ends and formed as thin plates, and the pushers can be arranged in the wave casing at an angle to a radial direction, and on the pushers the casings of sound-insulating material are arranged which adjoin the pushers along side end surfaces.

The rotor is formed of two thin-walled cylinders, which are arranged on an axial system, formed as a cylindrical sliding bearing of a sound-insulating material with a central flange, on which the thin-walled cylinders are fixed.

Mounting of the second piezoelement which is arranged on the body of the motor is formed as a rubber ring, arranged in a threaded slot in the body of the motor, a fluoroplastic ring arranged in a threaded slot in a pressing flange, and legs for connecting the pressing flange to the body of the motor, wherein the mounting of the first piezoelement arranged on the shaft of the motor is formed as a rubber ring located in the threaded slot on the flange, rigidly connected with the shaft, a fluoroplastic ring arranged in a threaded slot in the pressing flange, and legs for mounting the pressing flange to a flange which is fixedly connected with the shaft.

The housing of the drive is formed as a rigid square flange with cylindrical grooves, and is provided additionally with a casing, wherein the casing is formed as a rigid thick-walled cylinder which ends in an analogous rigid thick flange, fixedly connected with one another.

The shaft of the motor is installed in ball bearings, one of which is arranged in the body and the other arranged in the casing and extends outwardly from the side of the body.

The displaceable table is located in composite linear guides and connected with a drive through a screw-nut, wherein the micrometric nut is rigidly fixed on the movable table.

The movable table is formed as a working surface with setting points, and its opposite side has setting openings for the micrometric nut and a solid longitudinal beam with a setting surface extending perpendicular to the working surface of the table and parallel to the axis of the setting opening for the micrometric nut, while at the opposite side an analogous beam is arranged with the possibility of its preliminary orientation in a plane which is parallel to the plane of the table, wherein guides with the possibility of their preliminary orientation on the setting planes, perpendicularly to the plane of the table, are installed on both setting planes of each beam.

The guides of the movable table through the balls or rollers adjoin the side guides which are mounted on the planes of rectangular angles with the possibility of their preliminary orientation in these planes, while the angles are fixed by orthogonal planes on a frame with the possibility of their preliminary orientation in the plane of the frame. The frame is formed as a solid rectangular beam with a flange for mounting of the drive and side reinforcement ribs.

Adjoining of the side angles, drive and other elements with the frame is performed through special steps-soles, provided on the setting planes of the frame with the possibility of formation of inter-plane air gaps.

The screw adjoins the micrometric nut, and with its one end through a ball abuts against a removable beam fixed on the frame, and with its another end is connected with the shaft of the drive, wherein between a thread and elements of mounting of the screw to the shaft a flexible connection is provided in form of cutouts which form thin elastic plate-shaped elements with a thickness of 100 . . . 400 µm, which are offset relative to one another by 90°.

The movable table is pressed through a ball to the immovable beam by two symmetrical springs which operate for stretching, and with one end fixed on the immovable beam, and the other end fixed on the movable table.

The micromanipulator is additionally provided with a device for automatic switching off of the corresponding direction of rotation of the piezoelectric drive in extreme positions which is composed of two microswitches located on the frame along the axis of displacement of a cam fixed on the movable table, wherein each microswitch is connected to a corresponding annular piezoelement so that in an initial condition it commutates a circuit of excitation of the corresponding piezoelement, and opens the circuit of excitation of the corresponding piezoelement when the microswitch is triggered.

In addition, the same second micromanipulator is arranged on the first so that the axes of displacement of movable tables are perpendicular relative to one another.

In addition, the same third micromanipulator is arranged on the second so that all three axes of displacement of the movable tables are orthogonal. All micromanipulators adjoin one another through special steps-soles, which are formed on transitional elements, movable tables and frames, with the possibility of forming inter-plane air gaps.

The first micromanipulator is arranged on the movable vertical axle, which is mounted on a clamp so that its axis of displacement is directed along a transverse coordinate of the working table, and the adjoining of the miromanipulator with the axle is provided through the movable table.

The axis of displacement of the second micromanipulator is directed along the longitudinal coordinate of the working table and its adjoining with the frame of the first micromanipulator is provided through the movable table.

The axis of displacement of the third micromanipulator is directed vertically to the plane of the working table, and its mounting is provided through a rectangular beam with side reinforcing ribs, which adjoins the frame of the second micromanipulator and the frame of the third micromanipulator.

The movable table can be formed as an immovable beam which rigidly adjoins the shaft of the drive.

In addition, a second such micromanipulator is arranged on the movable table, wherein the shafts of the drives are perpendicular to one another.

In addition, the second manipulator is arranged on the movable table with an offset relative to the shaft, so that the shafts of the drives are parallel to one another.

In addition, a third micromanipulator is arranged on the movable table of the second micromanipulator so that the shaft of the third micromanipulator is orthogonal to the shaft of the second micromanipulator.

FIG. 1 shows a kinematic diagram of the micromanipulator-prototype and a block-diagram of its control (1—a movable table; 2—bearing guides; 3—a micrometric screw-nut; 4—an immovable coupling; 5—a piezoelectric drive; 6—a rotor; 7, 8—annular piezoelements; 9—pushers; 10—a generator of high frequency pulses of excitation of the piezoelements; 11—a controlled key; 13, 14—formers of duration of the packs of pulses of excitation of the piezoelements and frequencies of their proceedings correspondingly; 12—a power supply source).

FIG. 2 shows a kinematic diagram of the proposed micromanipulator and a block diagram of control of the micromanipulator (1—a movable table; 2—linear guides; 3—pressing springs; 4—a micrometric nut; 5—a screw; 6—a flexible connection; 7—a shaft of a piezo electric drive; 8—a piezoelectricdrive; 9—a rotor; 10, 11—annular piezoelements; 12—pushers; 13—a housing; 14—amplifiers; 15—controlled keys; 16—generators of high frequency pulses of excitation of the piezoelements; 17—blocks of forming of a layer of frequency of packs of pulses of excitation of the piezoelement; 18—blocks of forming duration of packs of pulses of excitation of the piezoelements; 19—joysticks, for example resistive; 20—a block of forming a singular pack of pulses of excitation of the piezoelements).

FIG. 3 shows diagrams of signals, which explain the operation of the proposed micromanipulator ($U_g$—a signal at the output of the generator 16 of high frequency pulses of excitation of piezoelements; $U_{Fstep}$—a signal at an output of a block 17 of forming of frequency of packs of pulses of excitation of piezoelements;

$U_{tu}$—a signal at the output of the block 18 of a former of duration of pulse packet of excitation of the piezoelements; $U_c$—a signal at the output of the controlled key 15; $U_{PE}$—a signal at the piezoelement; L—a microdisplacement of a movable carriage; φ—an angular microdisplacement of the shaft of the motor).

FIG. 4 shows a construction of a piezoelectric drive with a high-frequency mode of control, a high level of resolution and a minimal level of accompanying mechanical microfluctuations (1, 2—annular piezoelements; 3—wave casings; 4—pushers; 5, 6—thick-walled cylinders of a rotor; 7—an axial system of the rotor; 8—rubber rings; 9—a fluor plastic rings; 10—a housing; 11—a casing; 12—pressing flanges; 13—an axial flange; 14—a shaft; 15—bearings).

FIG. 4a shows a construction of a piezoelectric oscillator (1, 2)—an annular piezoelement formed as a ring-shaped resonator with a radial shape of oscillations; 3—a wave casing; 4—pushers; 16—a flat electrode; 17—a direction of polarization; 18—a thin-walled cylinder; 19—reinforcing ribs; 20—gaps; D—an exterior diameter of the ring-shaped resonator; d—an interior diameter of the ring-shaped resonator, h—a height of the ring-shaped resonator).

Figure 5:
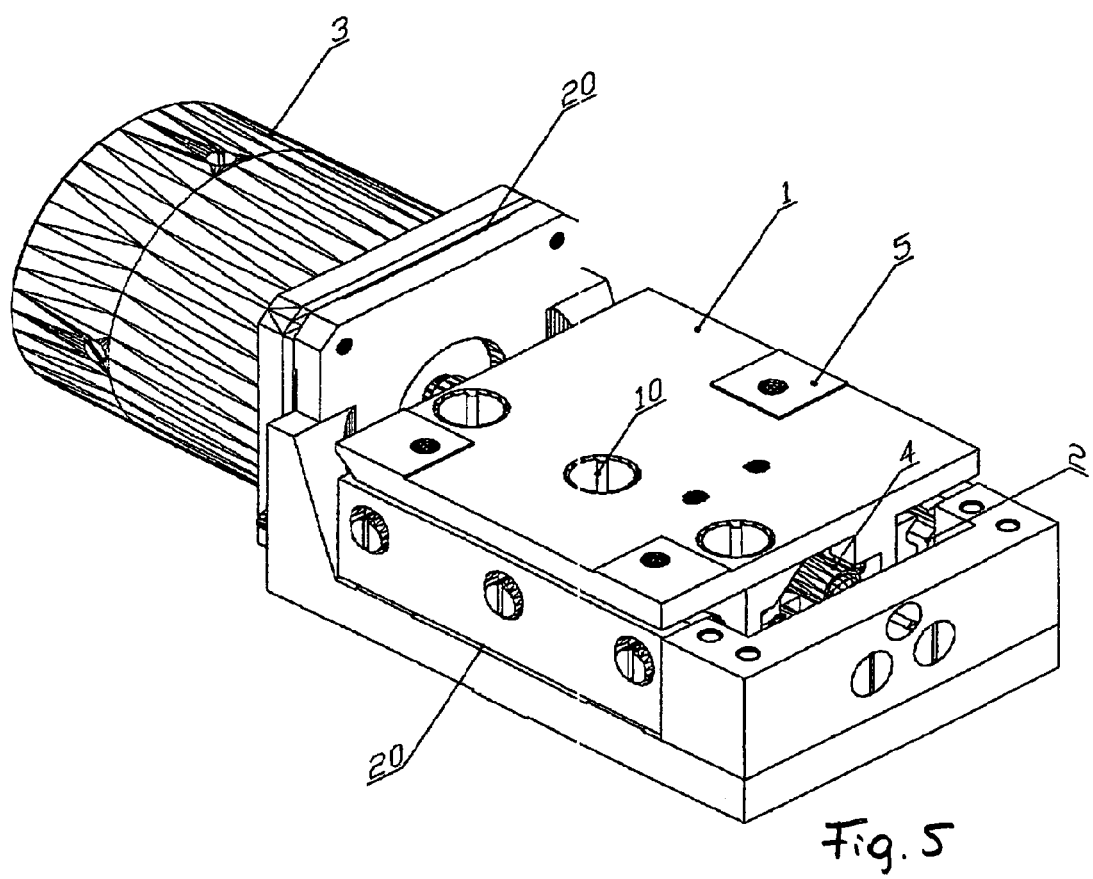
FIG. 5 shows a construction of a single-axis linear micromanipulator (1—a movable table; 2—linear guides; 3—a piezoelectric drive; 4—a precision screw; 5—setting spots; 10—setting screws; 20—inter-plane air gaps).
Figure 5A:
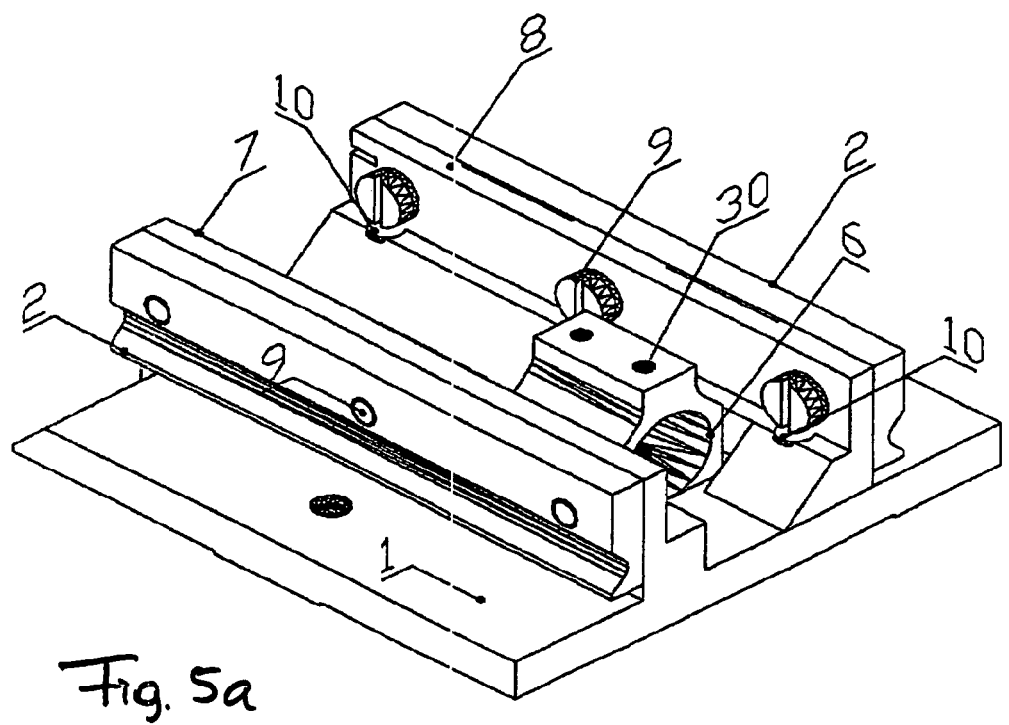
FIG. 5a shows a construction of a composite movable table (1—a movable table; 2—linear guides; 6—a setting opening for a nut with a screw; 7—a solid longitudinal beam; 8—a movable beam; 9, 10—setting screws; 30—setting openings for mounting of a cam).
Figure 5B:
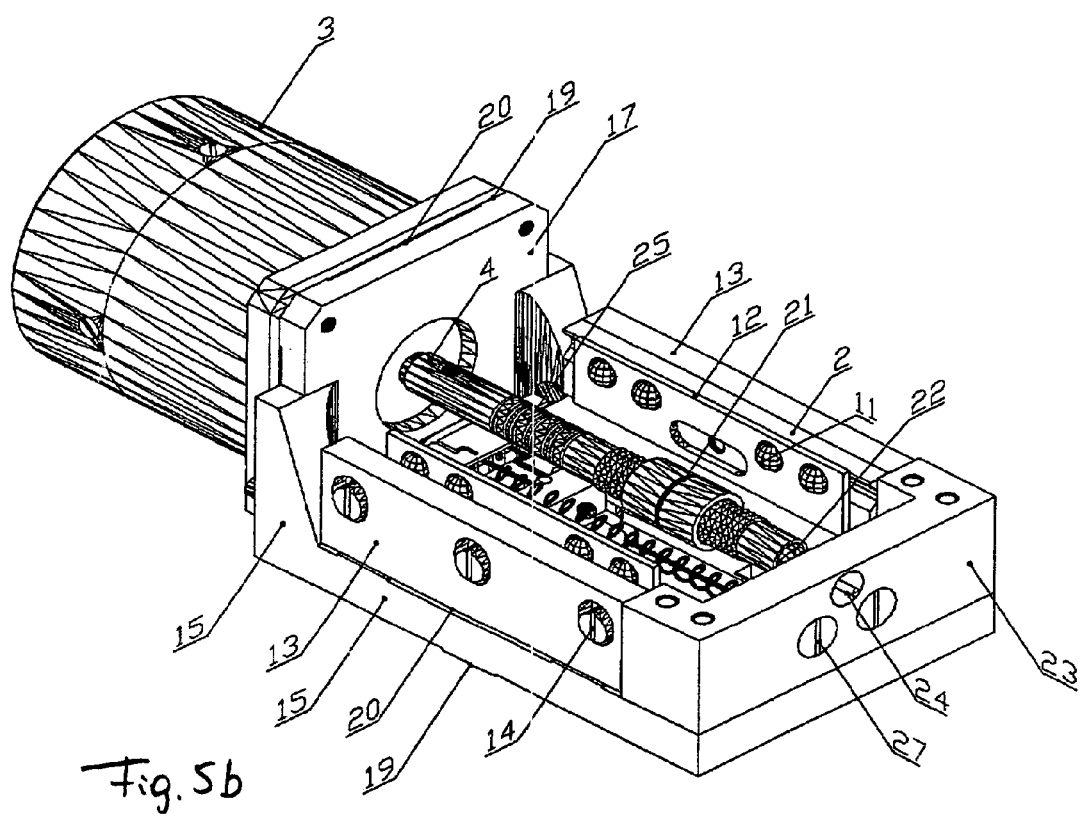
Figure 5C:
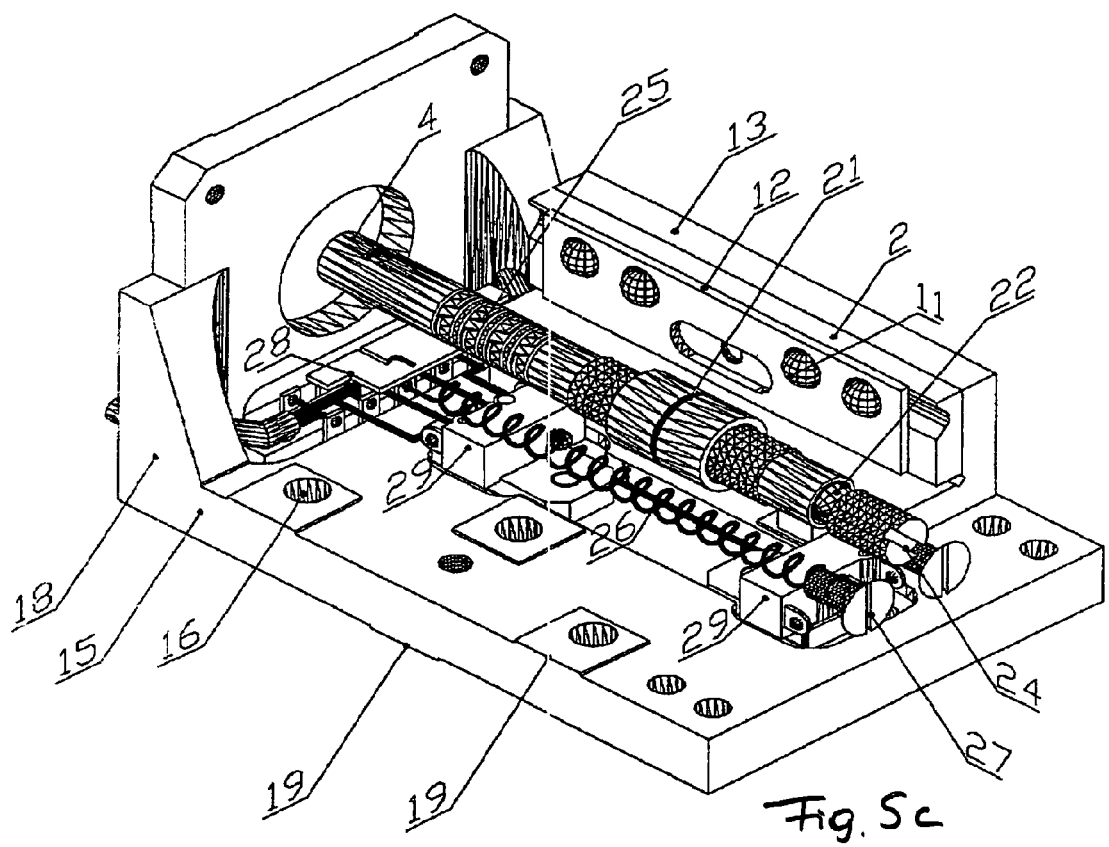

FIGS. 5b, 5c show elements of a construction of the linear micromanipulator (2—linear guides; 3—a piezoelectric drive; 11—balls; 12—a separator; 13—rectangular angles; 14—setting screws; 15—a frame; 16—openings in the frame for setting screws for mounting of angles; 17—a flange of the frame; 18—reinforcing ribs of the frame; 19—steps-soles; 20—inter-plane air gaps; 21—a precision nut; 22—a stop ball; 23—an immovable beam; 24—a backlash-compensating screw; 25—a flexible connection; 26—pressing springs; 27—a regulating screw; 28—a mounting beam for mounting of springs; 29—microswitches).

Figure 6:
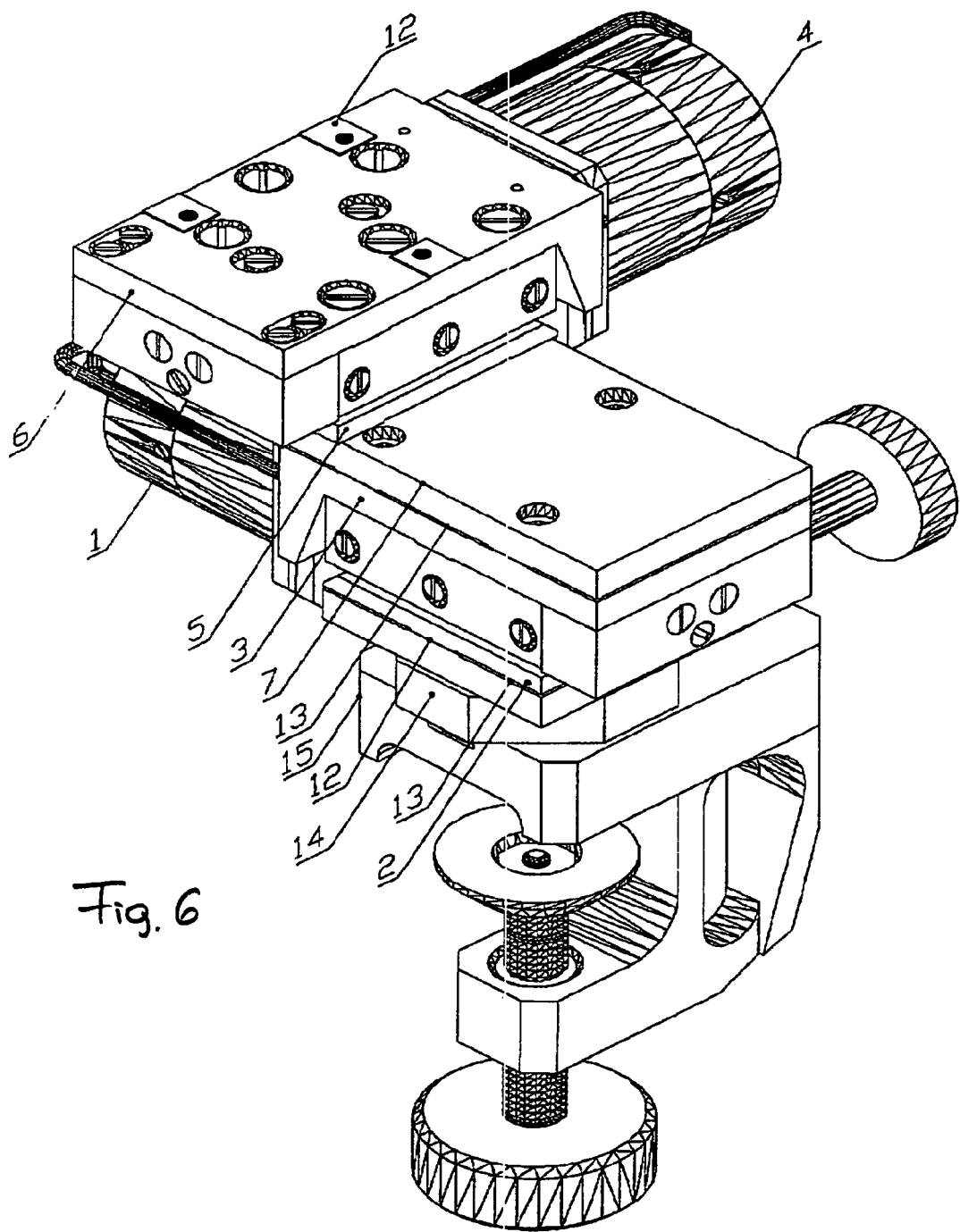

FIG. 6 shows a construction of a two-axes linear micromanipulator; (1, 4—piezoelectric drives; 2, 5—movable tables; 3, 6—frames; 7—a transition plate; 12—transition steps-soles; 13—interplane air gaps; 14—a vertical axis; 15—a clamp).

Figure 7:
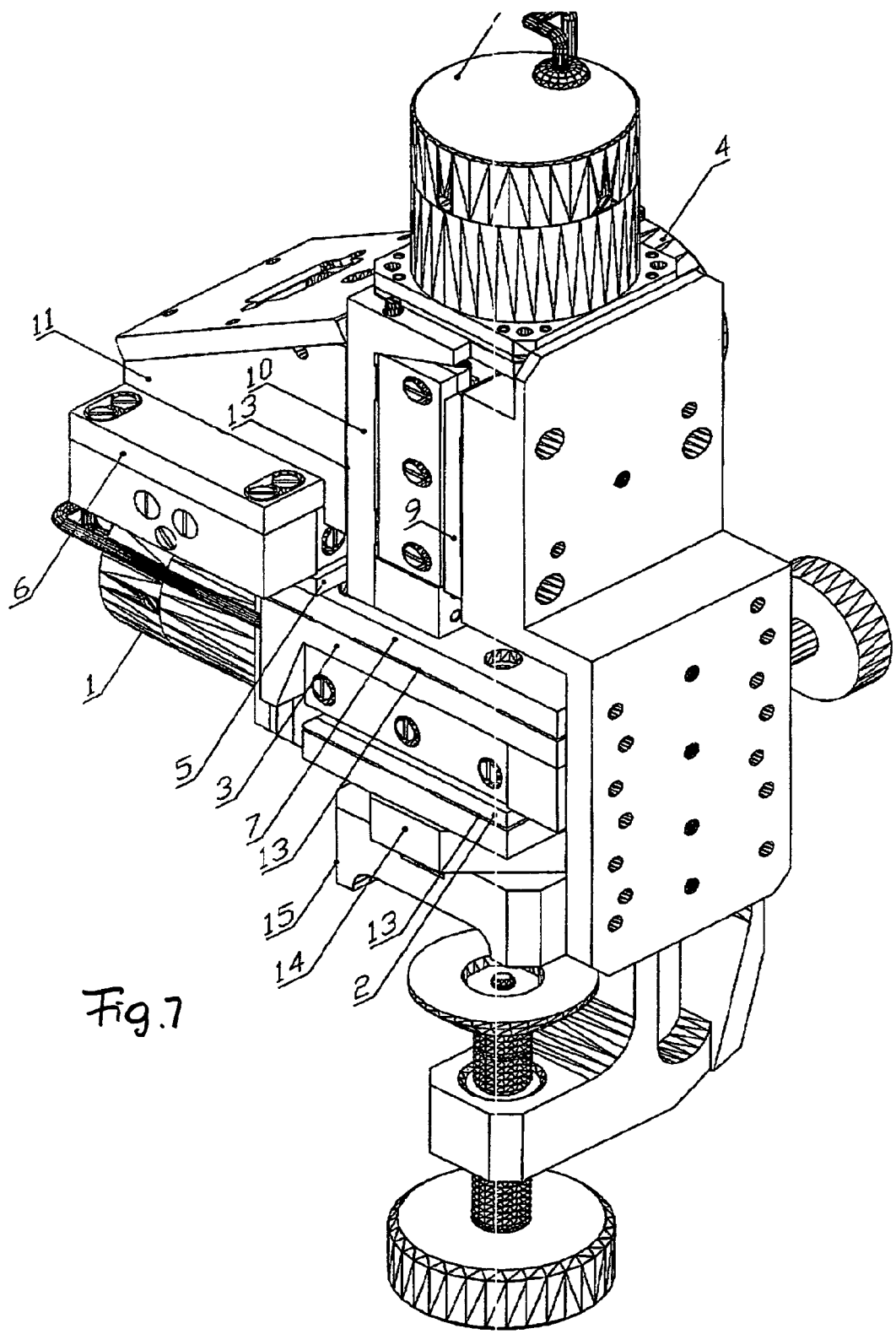

FIG. 7 shows a construction of a three-axes linear micromanipulator (1, 4, 8—piezoelectric drives; 2, 5, 9—movable tables; 3, 6, 10—frames; 7—a transition plate; 11—a transition rectangular beam; 13—inter plane air gaps; 14—a vertical axis; 15—a clamp).

Figure 8:
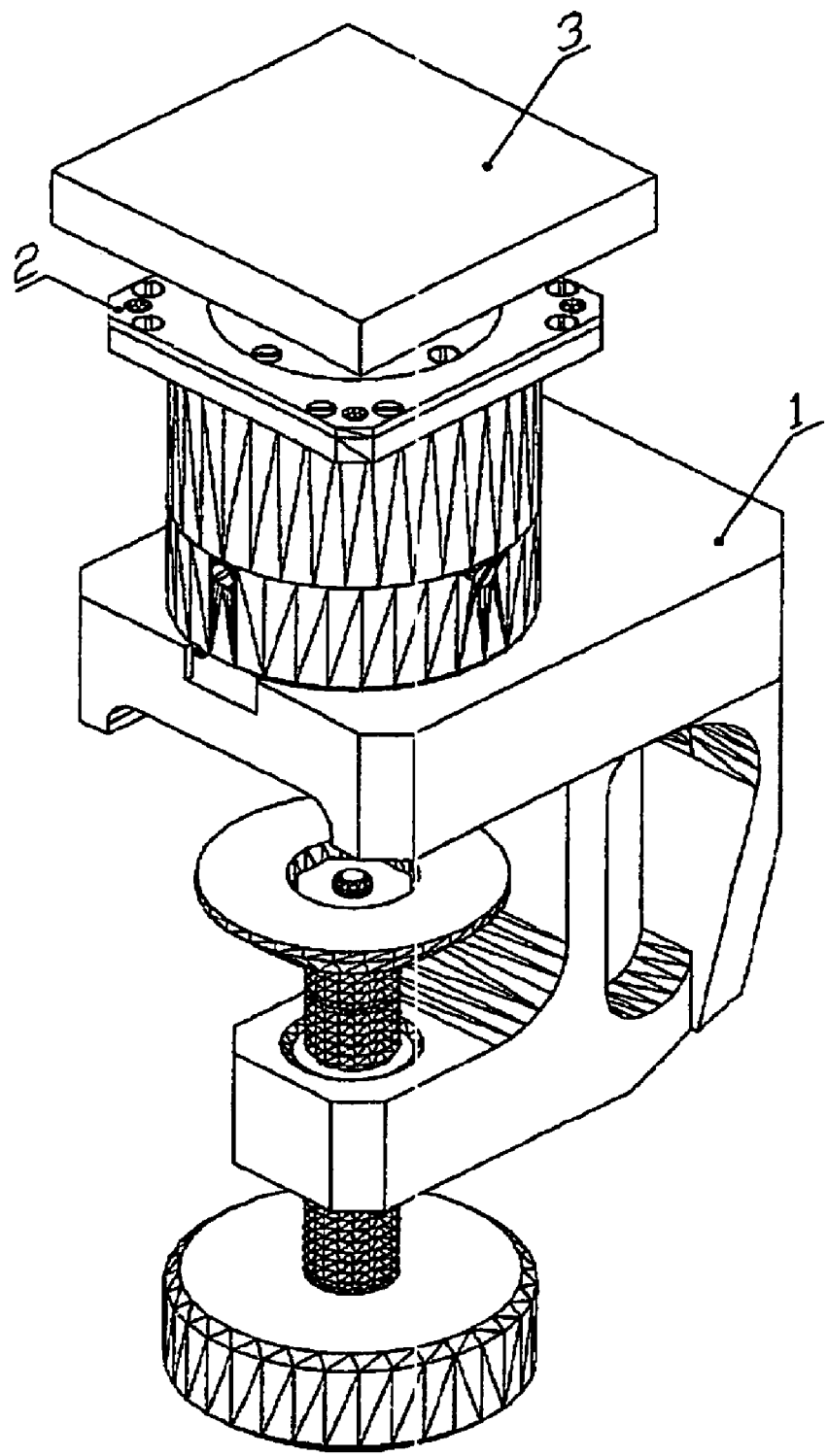

FIG. 8 shows a construction of a micromanipulator with one rotary degree of freedom (1—a clamp, 2—a drive; 3—a table).

Figure 8A:
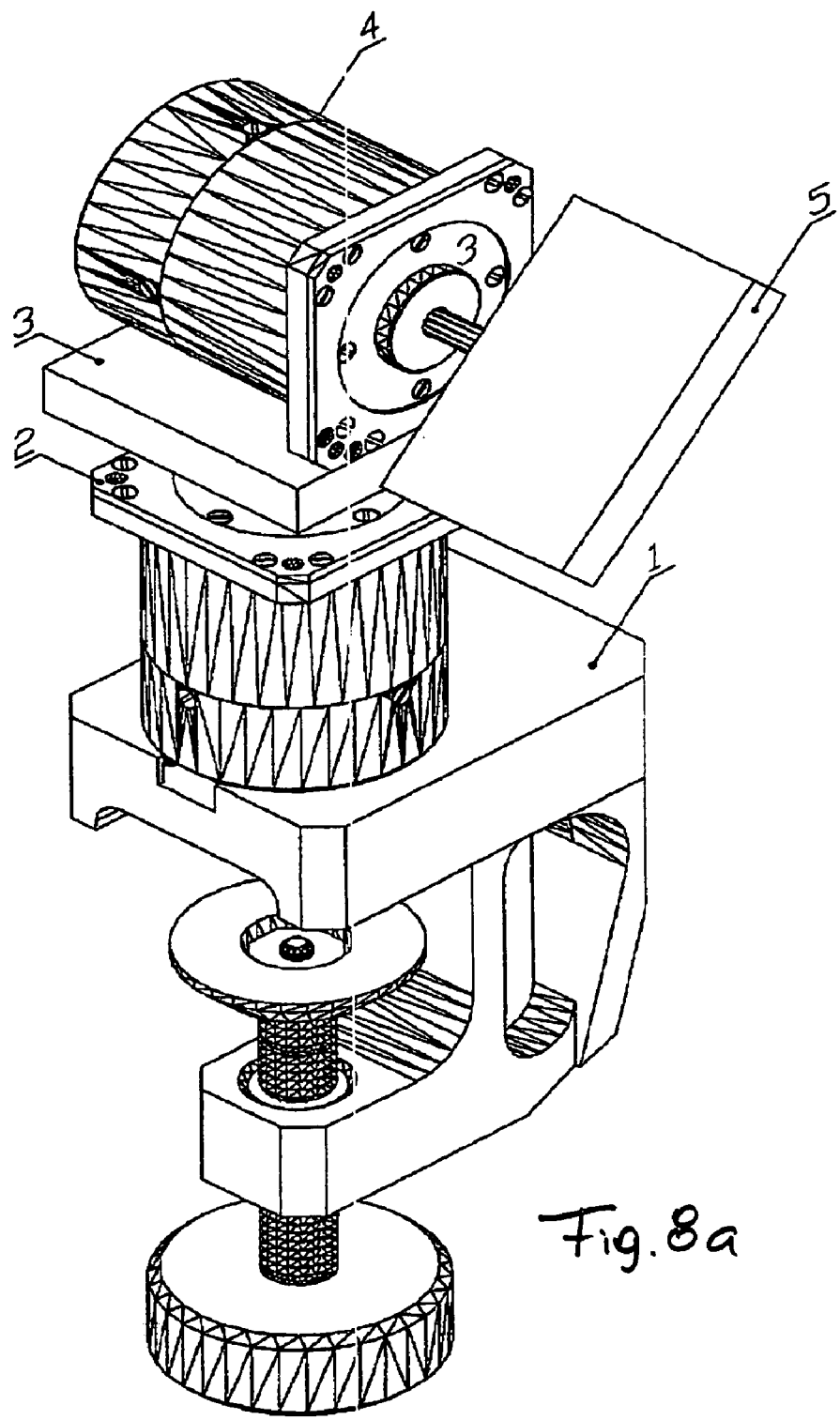

FIG. 8a shows a construction of a micromanipulator with two rotatable degrees of freedom (1—a clamp; 2, 4—drives; 3, 5—tables).

Figure 9:
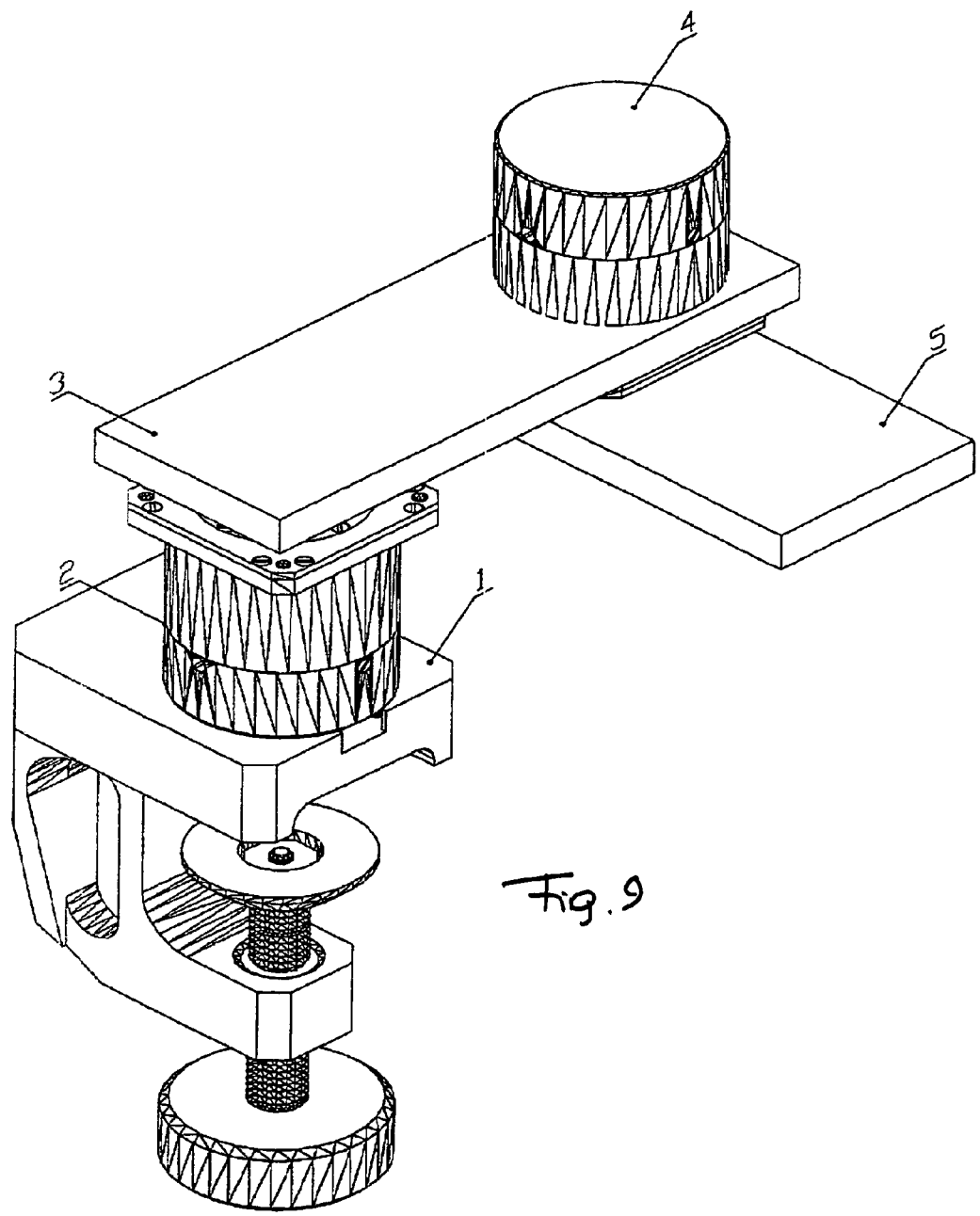

FIG. 9 shows a construction of a micromanipulator with a plane polar system of coordinates (1—a clamp; 2, 4—drives; 3, 5—tables).

Figure 9A:
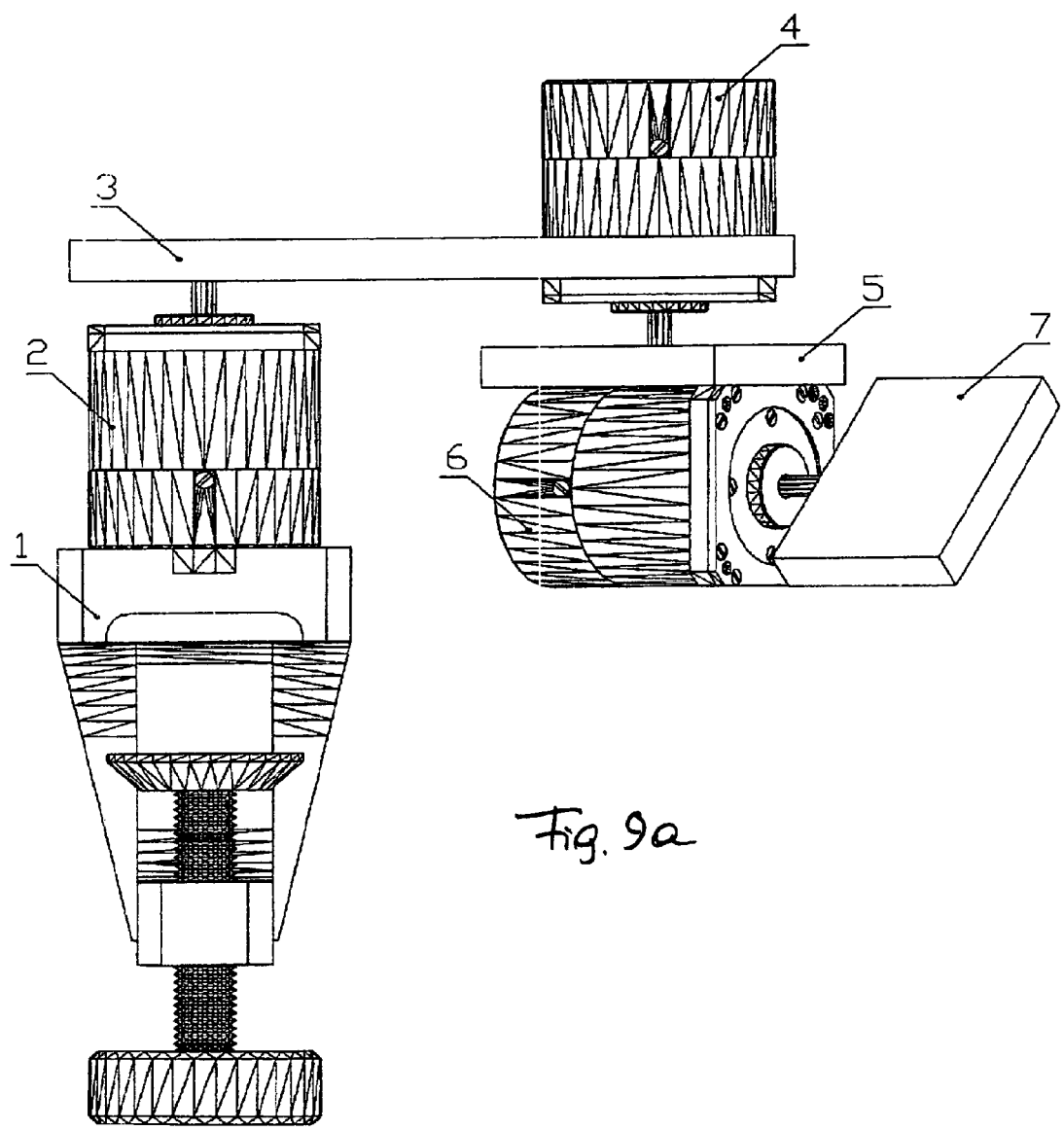

FIG. 9a shows a construction of a micromanipulator with a cylindrical system of coordinates (1—a clamp; 2, 4, 6—drives; 3, 5, 7—tables).

The essence of the proposed technical solution resides in a reduction of the level of accompanying mechanical vibrations and a simultaneous increase of resolution (accuracy), reduction of singular microdisplacements, expansion of a range of regulation according to a speed; expansion of functional possibilities of the micromanipulator due to complex scheme-technical and structural methods, connected with one another.

1. A scheme-technical method provides first of all a transition to a high-frequency area of control with formation of microdisplacements. The transition into the high frequency area involves an increase of frequency of preceeding of the steps, or, what is the same, of a frequency of packs of pulses of excitation of piezoelements.

It has been established experimentally that during formation of microdisplacements a frequency range which is free of vibrations starts at the frequency of proceeding of the steps F>2 kHz. With this control mode, a period of preceding of the steps must not exceed 500 micro seconds. However, a clear contradiction takes place, which is connected with superposition of extinguishing electric mechanical oscillations on the piezoelement from the preceding excitation and oscillations resulted from a new pack of excitation.

Since a piezoelectric motor is a resonance system with high quality, therefore the time of extinguishing of vibrations on the piezoelement $T_{EXT}$ usually is a few hundreds of micro seconds, and therefore a superposition of "old" (extinguishing) vibrations on "new" (exciting) oscillations takes place. A non-coincidence of phases of extinguishing and exciting oscillation leads to significant destabilization effects, which are accompanied by a detonation, vibration and strikes till stoppage of the motor and loss of functionality.

Figure 2:
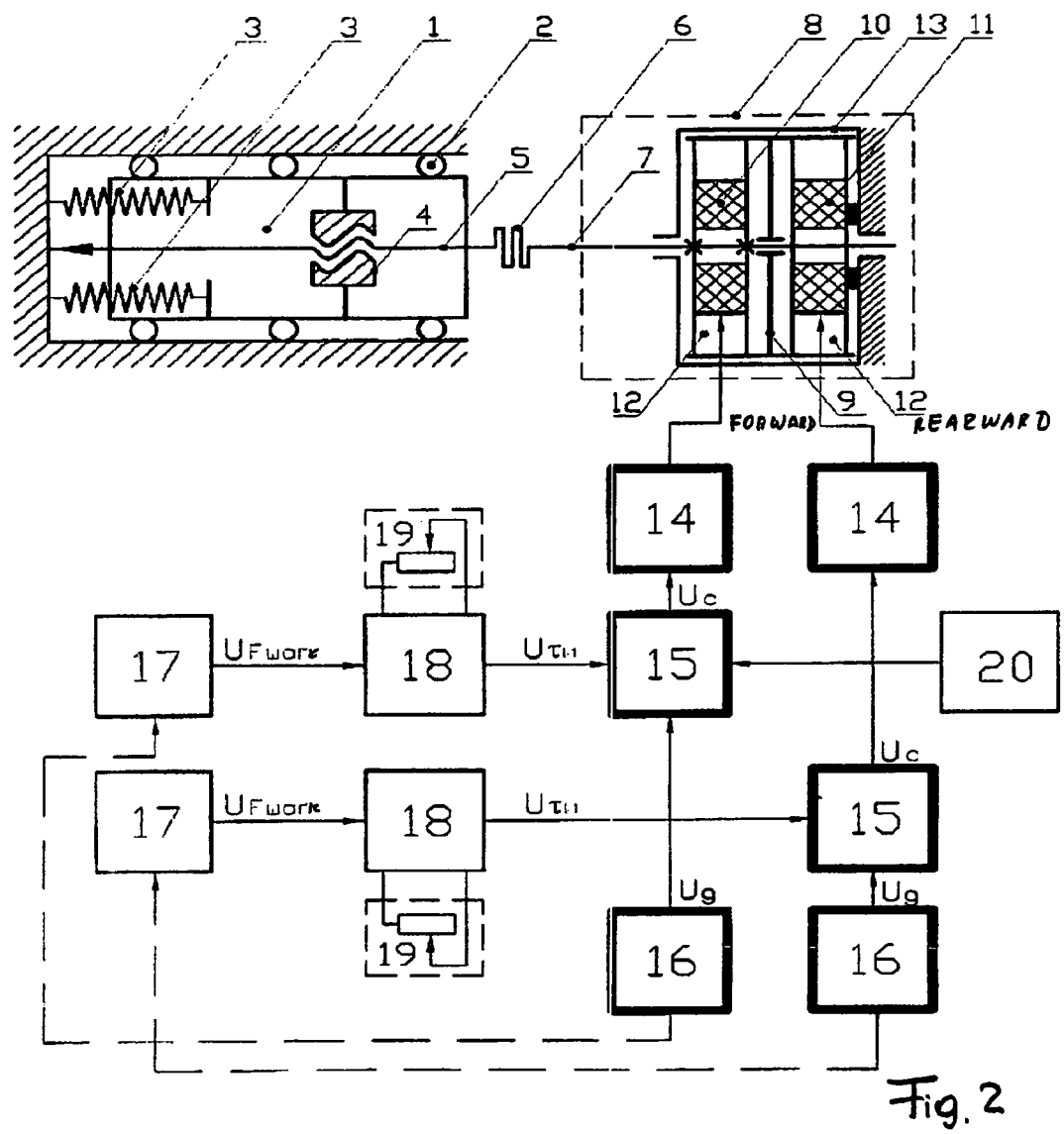

A stable operation of the micromanipulator during proceeding of the packs of excitation with the period $T<T_{EXT}$ is provided by means of the device shown in FIG. 2. The main principle which is used in this device is based on an uninterrupted monitoring of a phase of oscillations on the piezoelement and a synphase excitation of the piezoelement in correspondence with the controlled signal. This is achieved by means of the continuously operating generator 16 (signal $U_g$, diagram "A" FIG. 3), which is tuned on frequency $\nu_a$ of excitation of the piezoelement, and whose phase of oscillations always coincide with the phase of extinguishing oscillations on the piezoelement (signal $U_{PE}$, diagram "E" FIG. 3). The controlled key 15 in response to an exterior command passes the signal $U_g$ from the generator 16 or high frequency pulses of excitation of the piezoelement, i.e. forms a pack of excitation. Then a signal (pulses in a pack) is amplified by an amplifier 14 to a desired level and supplied to the piezoelement. On the corresponding piezoelement, for example piezoelement 10, radial oscillations are generated. Oscillations from the piezoelement are transmitted to the pushers 12, which are pushed from the lower piezoelement 11 of the rotor 9 which is frictionally-braked by the pushers, and generate a torque to the shaft 7. When the direction of rotation changes, the piezoelement 11 operates. During this process, the torque imparted by the pushers of this piezoelement to the rotor 9 is transmitted through the frictional contact of the pushers of the upper piezoelement 10 and farther to the shaft and load.

The step of the drive, or an angle of turning of the shaft $\Delta\phi$ is proportional to the duration of the pack of excitation $\tau_u$ or what is the same, to the duration of the control signal at the input of the controlled key. The angular microdisplacement by means of the micrometric screw 5 and the nut 4 is converted into a rectilinear movement which is transmitted to the movable table 1. During this process the micrometric screw is pressed by the spring 3 to the bottom and does not change its linear position, while the linear displacement is performed by the nut 4 which is fixedly connected to the movable table 1.

Thereby, the singular microdisplacement of the movable table $\Delta L$ is determined by a step of the drive and a ratio of screw-nut, while resulting speed with a given frequency of proceeding of the steps $F_{step} \geq 2$ kHz will be regulated by a change of the value of the step $\Delta L$, $\Delta\phi$. These functions are realized in the block 17 and 18. The block 13 forms the frequency $F_{step}$ of proceeding of the steps (signal $U_{Fstep}$, diagram "B" FIG. 3), while in the block 18 a duration of the pulses of control $\tau_u$ is formed in accordance with the frequency $F_{step}$ (signal $U\tau_u$ diagram "c" FIG. 3). The formed control signal is supplied to the controlled key 15, and the packs of pulses of excitation are supplied from its output on the resonance frequency of the piezoelement (signal $U_C$ diagram "D" FIG. 3). In this process in each subsequent cycle of excitation the phases of pulses in a new pack of excitation and extinguishing pulses on the piezoelement (signal $U_{PE}$, diagram "E" FIG. 3) coincide and this provides a stable operation of the system. The step of the piezodrive $\Delta\phi$ (or a singular microdisplacement $\Delta L$ of the movable table) is proportional to the duration of the control pulse $\tau_u$ (diagram "F", FIG. 3).

The speed of displacement with a given frequency of preceding of control pulses $F_{step}$, will be determined by a value of the microdisplacement $\Delta L$. By changing of $\tau_u$ a speed is changed. Therefore for comfort of control, a joystick is connected to the controlling input of the block 18, by means of which $J_u$ is changed. Conventionally resistive or optical joysticks are used in such systems. In the resistive joystick, deviations $\Theta$ (for example an angle of deviation) is conventionally proportional to a growth of resistance, or, what is the same, to the controlling signal. In the optical joystick, the deviation $\Theta$ is a linear deviation, for example a computer "mouse".

Two control modes can be used in the micromanipulator.

A first mode is when the duration of the pack of pulses of excitation $\tau_u$ is changed proportionally to the deviation of the handle of the joystick, or in other words $\tau_u = K \cdot \Theta$ (where K is a coefficient of proportionality). In this mode of control of micromanipulator, a speed changes gradually in a whole range depending on the deviation of the joystick.

A second control mode is when the duration of the pack of pulses of excitation $\tau_u = K \cdot \ln \Theta$ changes proportionally to a logarithm of deviation of the joystick handle, or in other words $J_u = K^* \ln 2$. In this non-linear mode of control, sensitivity of control from the deviation of joystick in the area of low speeds is increased, which is very important during micromanipulation with super small objects) and the sensitivity of control in the area of high speeds becomes cruder.

In order to form a starting phase connection of the pulses $U_{Fstep}$ from the block of forming of frequency 17 (diagram "B" FIG. 3) to the pulses on the piezoelement $U_{PE}$ (diagram "E" FIG. 3), an additional synchronization is introduced by the block 16 of the block 17, by means of introduction of an additional basic connection, that provides stability of step especially with low durations of a pack of pulses of excitation of the piezoelement.

For forming singular steps in an unlimited range to the block 15 (FIG. 2), a generator of singular pulses 20 can be connected with an unlimited range of change $\tau_u$ This mode is necessary for example for breaking through a membrane of cell during an internal injection, etc.

2. Structural methods provide first of all a transition to a construction of a piezodrive with a high frequency mode of control.

Figure 3:
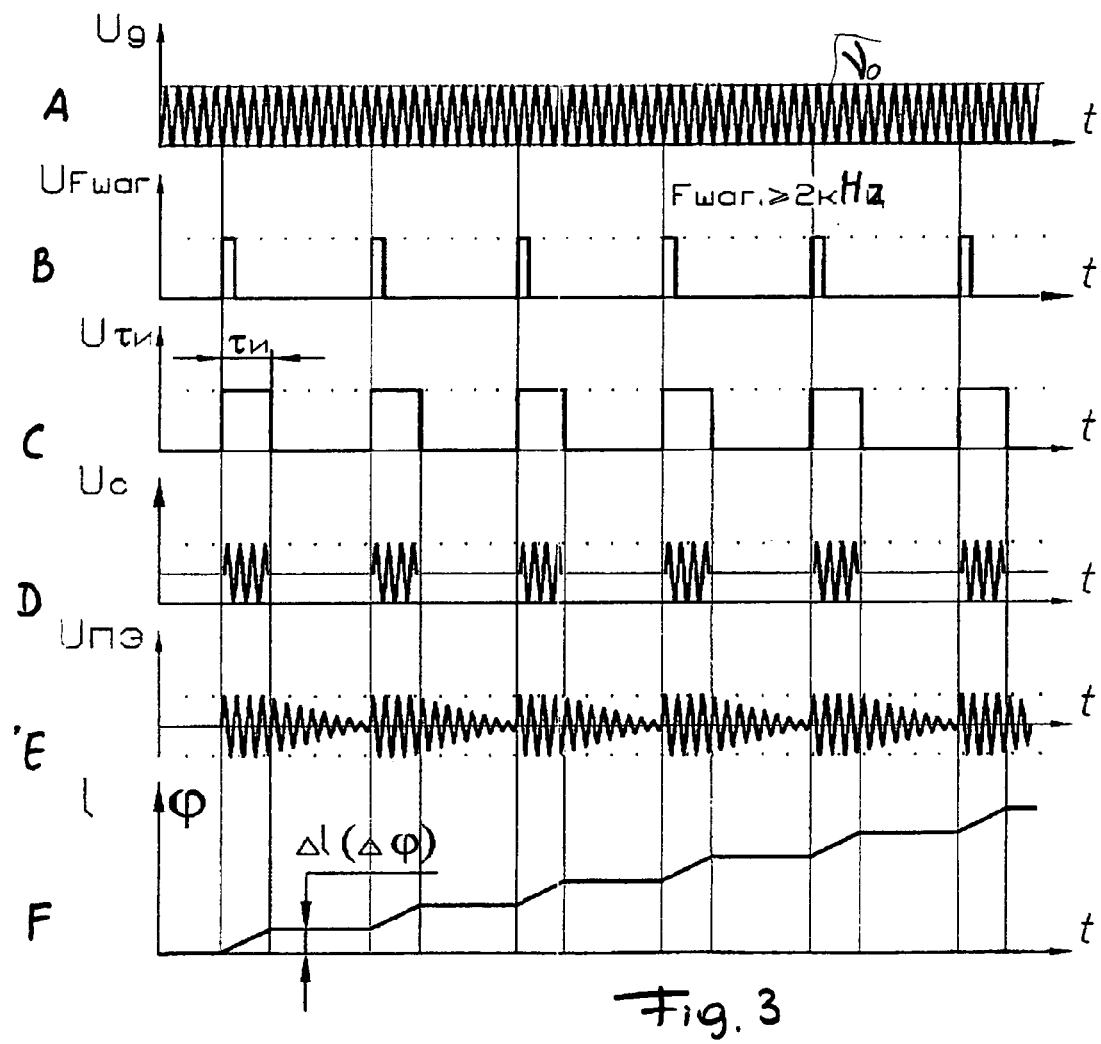

The high frequency control mode sharply reduces a range of regulation in accordance with speed. As mentioned above, with a fixed frequency of proceeding of steps $F_{step}$, the magnitude of speed changes by a change of magnitude of the step $\Delta L$ or in the system—by means of change of duration of the pack of excitation $\tau_u$ (FIG. 3). Therefore for the present case $F_{step} \geq 2$ kHz, the upper limit of regulation according to $\tau_u$ is limited by the value $\tau_u^{max} \leq 1/F_{step} = 500$ micro sec. In accordance with the speed this will be a mode of a continuous rotation or a maximum speed. A minimum speed of a microdisplacement will be determined by a minimum possible magnitude of an angular step of the drive $\Delta\phi_{min}$ while as small as possible value of $\tau_u^{min}$ must correspond to this value of the step.

Taking into consideration the required minimal speeds of microdisplacements (~0.5 μm/s), the required resolution (~0.001 μm) and a smoothness of regulation, it is possible to formulate main requirements for the piezoelectric drive with a high frequency mode of control:

minimal angular step (angular resolution))$\Delta\phi_{min}$~0.6 angular sec (modern level in corresponding sizes ~10 angular sec);

for a given angular step $\Delta\phi_{min}$ a duration of the pack of excitation $\tau_u^{min}$ micro sec (modern level ~150 . . . 200 micro sec) must correspond;

minimal level of accompanying vibrations during the operation of the piezoelectric drive.

Figure 4:
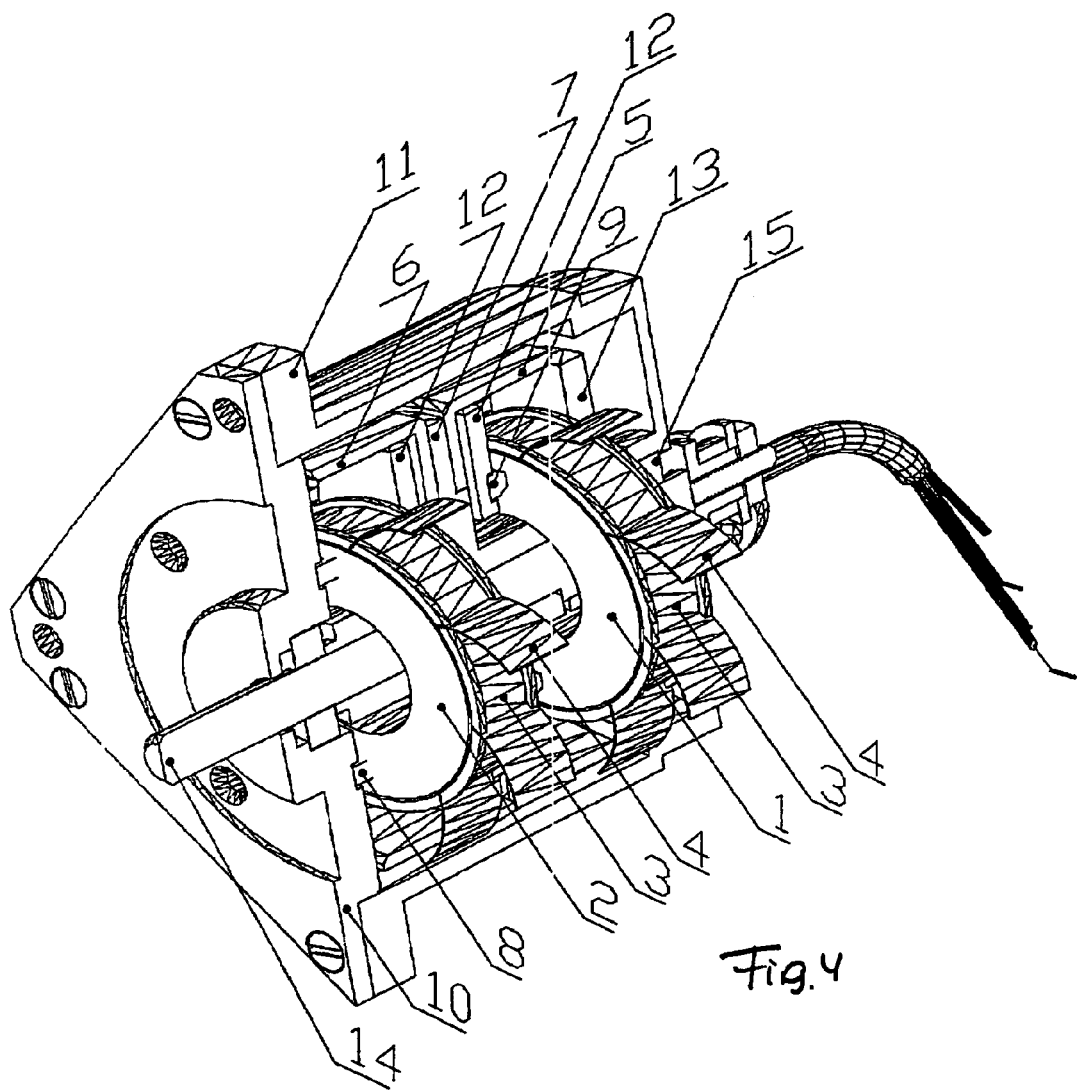
FIG. 4b shows a construction of a rotor of the piezoelectric drive (5, 6—thin walled cylinders; 7—an axial system; 21—cylindrical sliding bearings; 22—a central flange).
FIG. 4c shows a construction of an oscillator with sound-insulating casings (1—annular piezoelement; 7—a wave casing; 4—pushers; 23—noise-insulating casings or ballasts).
FIG. 4d shows a construction of a unit for mounting of the immovable annular piezoelement 2 to the body of the drive (2—annular piezoelement; 8—a rubber ring; 9 a fluoro plastic ring; 10—a body; 12—a pressing flange; 15—a ball bearing; 24, 25—cut fixing slots; 26—mounting legs; 28—an inner cylindrical groove; 29—an exterior cylindrical groove).
FIG. 4e shows a construction of a unit of mounting of Movable annular piezoelement to the shaft of the drive (1—an annular piezoelement; 8—a rubber ring; 9—a fluoro plastic ring; 12—a pressing flange; 13—an axial flange; 14—a shaft; 15—a ball bearing; 25, 27—cut fixing slots; 26—mounting legs).

The proposed construction of such a piezoelectric drive is shown in FIG. 4. Such a piezoelectric drive operates on radial oscillations, and therefore the annular piezoelements 1, 2 are formed in the form of ring-shaped resonators with a radial shape of oscillations.

The process of formation of angular microdisplacements with a subsequent their maintenance in the proposed drive can be conditionally subdivided into two subprocesses: a process of formation of resonance ultrasound radial oscillations in a ring-shaped resonator, and a process of transformation of these oscillations into a single-direction microdisplacement of a rotor.

The first process in the order of cause-result connection—is a process of formation of resonance ultrasound radial oscillations in a ring-shaped resonator. With the radial shape of the oscillations, an axial line remains a circular line with a periodically changed radius, while a set of own frequencies $v_m$ can be determined in accordance with the ratio (Machinebuilding Guide, Edited by S. V. Serensen, Publishing House Machine Building Literature, Moscow 1962, volume 3, page 417):

$$v_m = \frac{1}{2\pi}\sqrt{\frac{E}{p_2 R_2}(1+m^2)}, (m=0,1,2,3...),$$

wherein E—is a Young modulus of the material of piezoelement;

R—is a median radius of a ring of the piezoelement;

$p_2$—is a density of the material of the piezoelement;

m—is a number of a mode of oscillations.

It has been established experimentally that in a high-frequency control mode, the drive operates most efficiently on a zero mode (m=0), since in this mode it is possible to reach a maximum amplitude of oscillations (~0.01 . . . 1.0 μm) on the exterior cylindrical side of the ring-shaped resonator, and therefore to provide a stabile triggering of "start" of the drive. However, in order to provide a necessary duration of the triggering of the "start", this mode must be within the range 50 . . . 120 kHz, which is determined by sizes of the resonator. On the one hand, this system must have a unique braking "stop" characteristics. For this purpose, as has been determined experimentally, the time of attenuation of oscillations in the ultrasound range of excitation must be counted with 5 . . . 10 periods of excitation, which, being recalculated to the quality of the resonator, $Q=\pi\sigma_o\tau$ (wherein $\tau_o$ is own frequency of excitation, $\tau$—a time of attenuation of the oscillations e times) must correspond to the magnitude ~1 . . . 10.

In order to excite in the ring-shaped resonator radial modes of oscillations, it must have a certain axis-symmetrical configuration. This is especially important for minimization of the piezoelectric drives, and therefore the resonators as well. The experimentally established parameters for the ring-shaped piezoelectric resonators with an exterior diameter D≦20 mm include: D/d~2; d/2~h (wherein d is an interior diameter of a ring-shaped resonator, h is a height of the ring-shaped resonator), that corresponds to a thick ring, for example φ20*φ10*5. On the other hand, a uniform ultrasound deformation along the whole ring must be excited in such a resonator. This is achieved by a flat system of electrodes formed on the flat end surfaces and by polarization along a normal to the end surfaces, FIG. 4a.

The external cylindrical surfaces of the piezoelement are embraced by wave casings 3 on which pushers 4 are mounted and press against the inner surface of the cylinders 5, 6 of the rotor, FIG. 4. Primary radial oscillations, being transformed in the wave casing and in the pushers perform microdisplacements of the rotor.

Figure 4A:
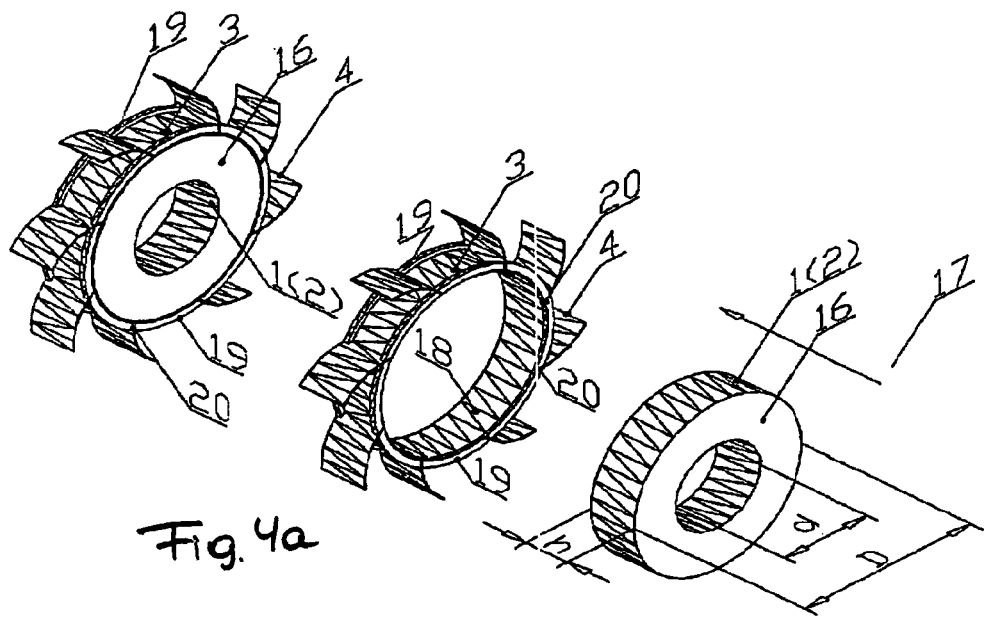

The wave casing, FIG. 4a, is formed as a metallic thin-walled cylinder 18 with fields which are turned from both sides and form ring-shaped reinforcing ribs 19, wherein the above mentioned reinforcing ribs are cut by slots 20, in which plate-pushers 4 are mounted with one end. This configuration of the wave casing provides a splitting of a zero mode of radial oscillations $v_o$ into two components—a low frequency component $v_o''$ and a high frequency component $v_o^v$ which are spaced from one another by 1-3 kHz. It is determined experimentally that $v_o^v$ corresponds to a resonance of a moment ($v_o''$—a resonance of speed), and with the frequency $V_o^v$ it is possible to reach a significantly smaller angular step and smaller duration of pulses of excitation $\tau_u^{min}$. Therefore the frequency of the generator 16, FIG. 2, usually corresponds to $v_o^v$.

The second process performs a conversion of the oscillating movement into a one-direction microdisplacement of the rotor due to the excitation in the pushers of oscillations along two mutually-perpendicular directions. In this case, the radial oscillations of the resonator and the wave casing are transformed into longitudinal oscillations of the pushers, while a transverse bending oscillations are excited in a mechanical way due to interactions of the pusher with the surface of the rotor, against which they abut at an acute angle and press with the force P. This force forms, on a certain radius of the rotor, a moment of self-braking $M_{self}$ which maintains the microdisplacements and forms static "stop" characteristics. A moment of selfbraking for obtaining a resolution in micron and submicron ranges, which is determined experimentally must be at the level ~0.08 . . . 1.00 N*m. This moment of selfbraking in corresponding sizes can be provided only with an exterior location of the pushers FIG. 4a, under the condition of their abutment against the inner surface of the rotor. When the two mutually perpendicular oscillations are superposed with an identical frequency, determined by a frequency of excitation of the resonator, a point of contact of the pusher with the rotor start moving along a flat elliptic curve, whose part is located on the surface of the rotor, so as to transmit to it a one-direction pulses of microdisplacement.

Figure 4B:
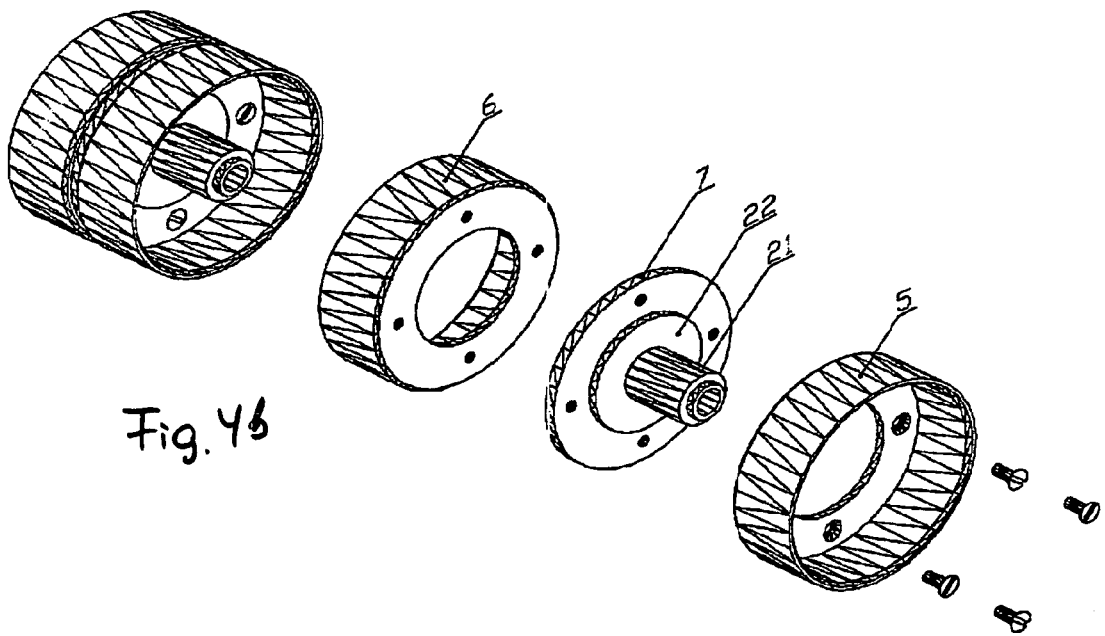

The dynamics of forming of the angular step under the action of these pulses of microdisplacement involves portions of speeding and braking, which are determined first of all by inertia properties of the movable elements of the drive. It is not difficult to show that the most inertial link is the rotor. Therefore, for minimization of inertia properties of the rotor, the pushers in the proposed drive are located at an angle, FIG. 4a, FIG. 4c (slots 20 are cut at an angle to the radial direction), which allows to reduce the diameter of the rotor, so as to bring its inner surface closer to the wave casing. For the purpose of reducing the mass, the rotor is composed of two thin-walled cylinders 5, 6, which are placed on a light axial system 7 (FIG. 4, FIG. 4*b*). All these measures, in a complex, allow to reduce an inertia moment of the rotor, and therefore to increase the resolution of the system.

The performed evaluations show that with the frequency of excitation $v_o$~70 kHz, amplitude of excitation ~0.5 µm, a total moment of self-braking $M_{self}$~0.1 N*m, the inner diameter of the rotor ~30 mm, a minimal angular step was $\Delta\phi_{min}$ angular sec at $\tau_u^{min}$ microseconds which well corresponds to the experiment.

Figure 4C:
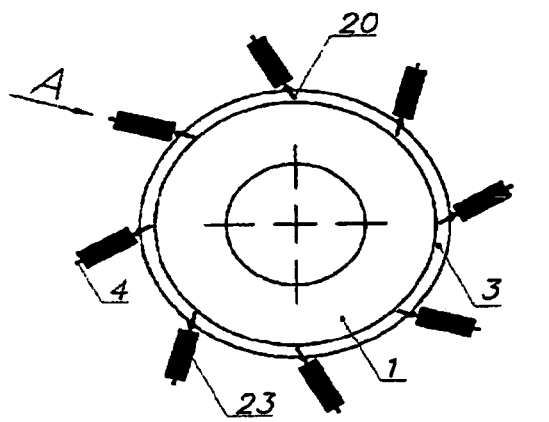
Figure 4C:
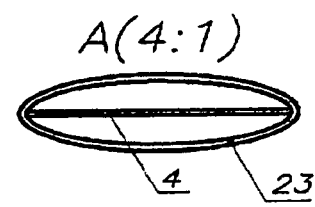
Figure 4C:
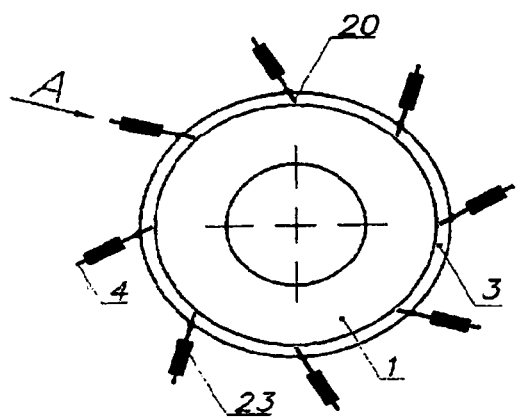
Figure 4C:
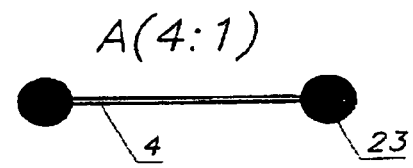

For the purpose of minimization of the level of harmful low frequency oscillations on the rotor and on the drive as a whole, which are created on the pushers and accompany the working high frequency oscillations, casings and ballasts 23 of a sound insulating material can be arranged on the pushers, for example of rubber or polyvinylchloride, FIG. 4*c*. However, these casings must not influence the propagation of the longitudinal working ultrasound oscillations in the pusher. Therefore the adjoining of the casing or the ballast with the pushers is performed along the side surfaces of the pushers FIG. 4*c*.

For the purpose of insulation of ultrasound vibrations of the rotor from the shaft of the motor, and also of one working part of the rotor from another, the rotor is formed as a composite rotor (FIG. 4*b*). The elements of the rotor (thin-walled cylinders 5, 6) adjoin one another through an axial system 7, which is formed as a cylindrical sliding bearing 21 with a central flange 22 of a sound insulating material, for example capralon, for fixing of the cylinders. It was confirmed experimentally that such a construction and arrangement of the rotor considerably reduces the level of accompanying microinterferences during the operation of the piezoelectric drive.

Figure 4D:
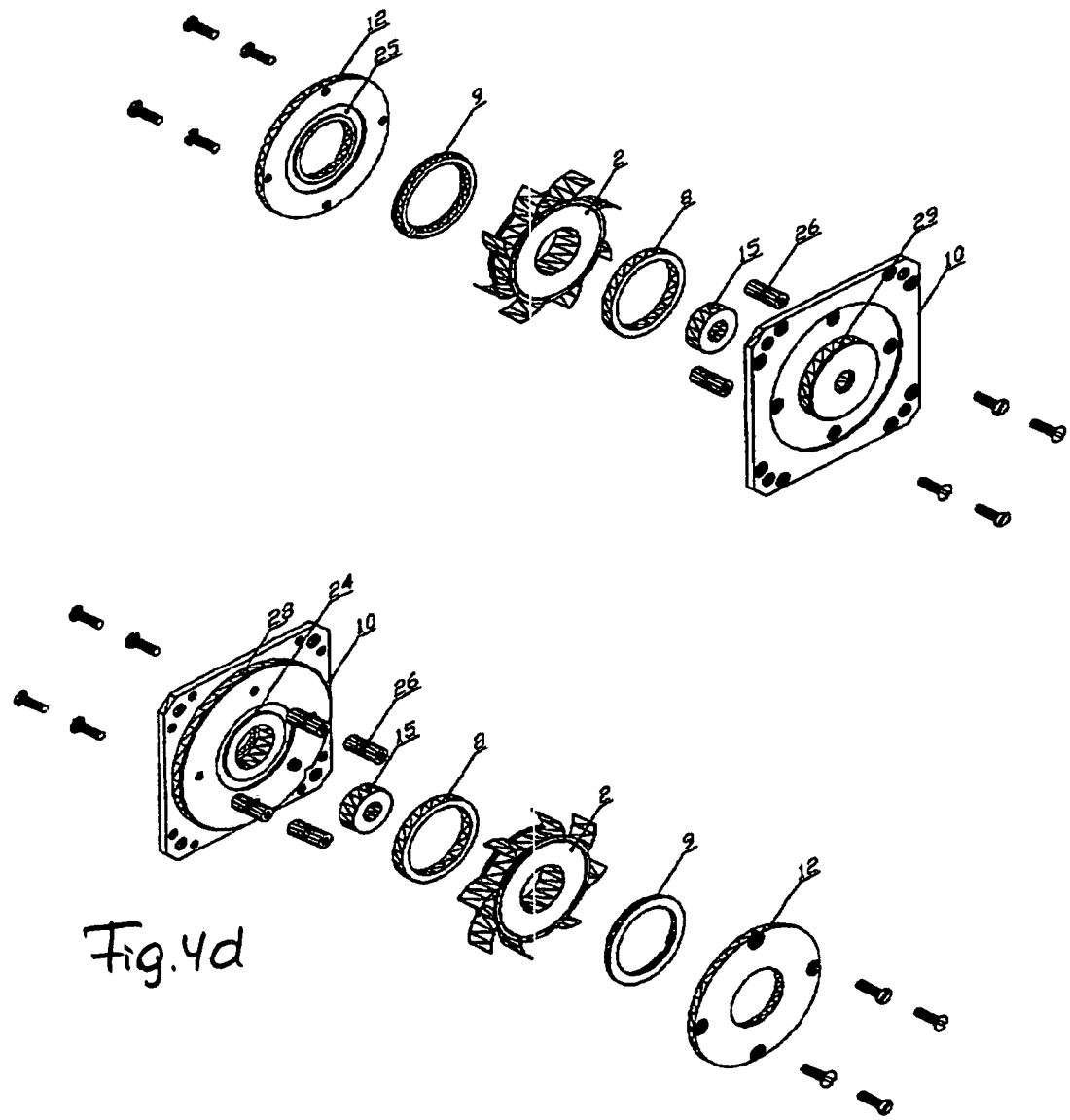

For the purpose of insulation of ultrasound oscillations of the second annular piezoelement from the housing of the drive, and also for providing the required rigidity of fixation, to eliminate gap in the drive and to increase the accuracy, the unit of fixation of the annular piezoelement 2, FIG. 4, FIG. 4*d* arranged on the housing 10, is formed as a rubber ring 8 which is mounted in the threaded fixing slot 24 in the housing 10, a fluoroplastic ring 9 arranged in a threaded fixing slot 24 in a pressing flange 12, and fixing supports 26 of the pressing flange 12 to the housing of the drive. The rubber ring provides an ultrasound insulation in a wide spectrum of frequencies, while the fluoroplastic ring provides a rigid holding of the piezoelement during the process of its operation, and at the same time does not influence the parameters of oscillations of the resonator (maintaining its degrees of freedom) due to "sliding" properties of the fluoroplastic. Such a structural combination of rubber and fluoroplastic allows to provide a high level of resolution of the drive with the simultaneous insulation of the housing of the drive from ultrasound vibrations.

Figure 4E:
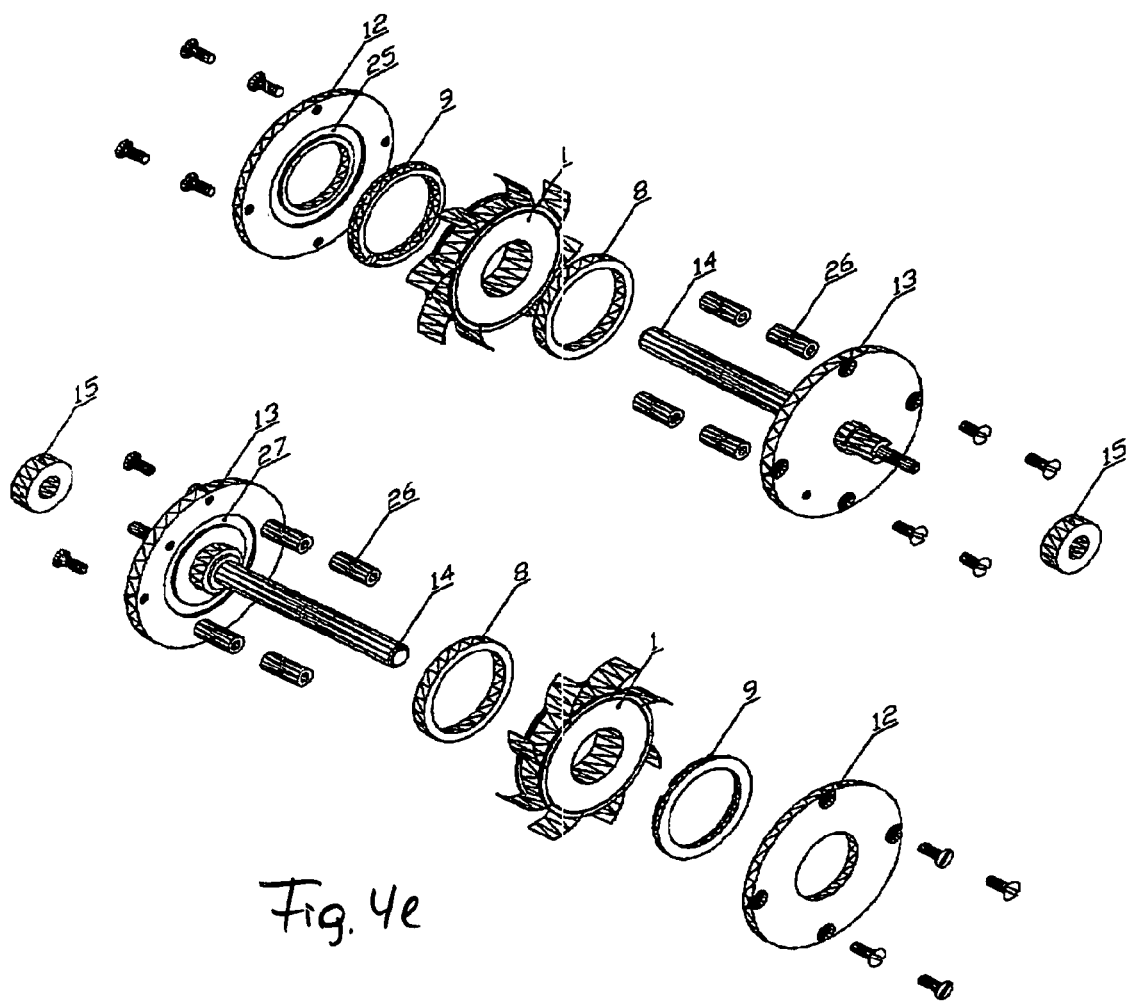

For the purpose of insulation of the ultrasound oscillations of the first annular piezoelement from the shaft of the drive, and also to provide the required rigidity of the connection to eliminate gap in the system, the unit of fixating of the ring-shaped piezoelement 1, FIG. 4, FIG. 4*e*, arranged on the shaft 14 of the drive, is formed as a rubber ring 8 arranged in a threaded fixing slot 27 in the axial flange 13, pressed on the shaft, a fluoroplastic ring 9 arranged in a threaded fixing slot 25 in the pressing flange 12, and fixing supports 26 of the pressing flange 12 to the axial flange 13 of the drive. The rubber ring provides ultrasound insulation of the axial flange, and therefore the shaft, in a wide spectrum of frequencies, while the fluoroplastic ring provides a rigid holding of the piezoelement during the process of its operation and simultaneously does not influence the parameters of oscillations of the resonator (maintaining its degree of freedom) due to "sliding" properties of fluoroplastic. Such a structural combination of rubber and fluoroplastic allowed to provide a high level of resolution of the drive with a simultaneous insulation of the shaft of the drive from ultrasound vibrations.

For the purpose of reduction of ultrasound oscillations of the body and accompanying microinterferences during the operation of the piezoelectric drive, the housing of the drive is formed as a rigid square flange 10, with cylindrical grooves 28, 29, FIG. 4, 4*d*, and a casing 11 is formed as a thick-walled cylinder that ends with an analogous rigid thick flange connected with the housing. Such a combination of square and cylindrical contours creates a high dynamic resistance to acoustic oscillations of a low frequency and ultrasound ranges and therefore significantly reduces microinterferences on the housing during the operation of the piezoelectric drive.

For the purpose of minimization of ultrasound oscillations of the shaft, by its insulation from the housing, the shaft 14 is arranged in ball bearings 15, one of which is located in the housing 10, FIG. 4, FIG. 4*d*, and the other is arranged in the casing 11, FIG. 4, FIG. 4*e*, while the working part of the shaft extends outwardly beyond the side of the housing of the drive. The use of the ball bearings is selected due to lower transmission of ultrasound oscillations to the shaft, and their distance in a space allows to uniformly distribute load along the whole shaft, to increase its radial rigidity and therefore the accuracy of the drive. The exit of the working part of the shaft from the side of the housing, allows to reduce ultrasound vibration of the shaft due to increased rigidity of the housing on the one hand, and on the other hand due to the structural distance of the main source of ultrasound oscillations to a shaft-annular piezoelement 11.

3. The structural methods also involve a transition to a construction of a vibro insulated guide with an increased accuracy.

The construction of the movable table of the micromanipulator is determined by its functional objective (linear and rotary microdisplacements) and can be realized with different methods.

Figure 1:
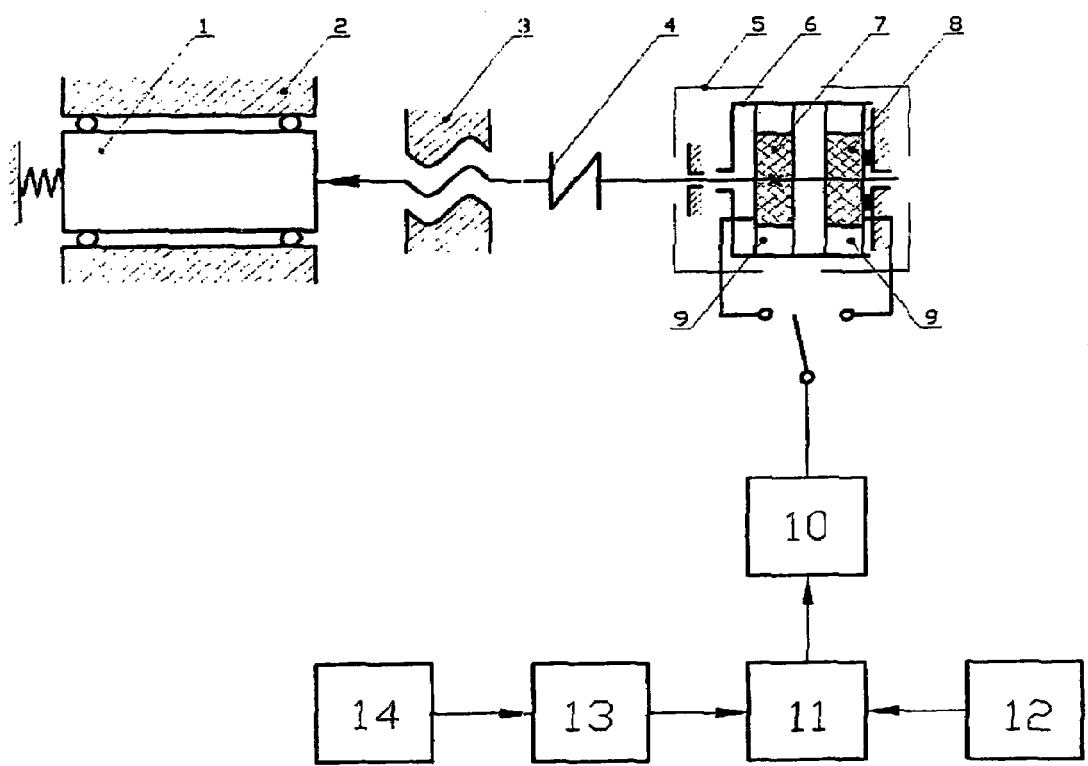

The proposed construction of the linear manipulator, FIG. 5, includes a movable table 1 in linear guides 2 (for example ball guides), wherein the movable table 1 is connected with a piezoelectric drive 3 through a precision screw with the nut. The micrometric nut is located on the movable table 1, FIG. 2, which excludes a movable coupling 4, FIG. 1, (a source of an additional backlash) and allows to transit to a backlash-less flexible connection 6, FIG. 2.

For increase of accuracy of the guide and simultaneous reduction of the level of accompanying mechanical interferences during the operation of the drive, the guides are formed as composite guides (since composite constructions have greater damping of ultrasound oscillations due to frictions in microgaps), with elements of increased rigidity and vibro insulation.

For this purpose the movable table 1, FIG. 5, FIG. 5*a*, is formed as a working surface with setting spots 5, with a setting opening 6 at an opposite side for a micrometric nut with a screw and an integral longitudinal cantilever 7 with a setting surface which is perpendicular to the working surface of the table and parallel to the axis of the setting opening 6 for the nut with the screw, and on the other side with an analogous cantilever 8 arranged with a possibility of its preliminary orientation in a plane which is parallel to the plane of the table wherein guides 2 are arranged on both setting surfaces of each cantilever with the possibility of their longitudinal orientation on the setting planes perpendicular to the plane of the table. The accuracy of the guide is determined first of all by the accuracy of mounting of the guides 2 in a space (their parallelism). This is achieved by their relative mounting during assembly (a preliminary turning and displacement in planes perpendicular to the plane of the table) on the setting planes by means of screws 9, and preliminary mounting during assembly of the cantilever 8 (a preliminary turning and displacement in a plane parallel to the plane of the table) by means of screws 10, FIG. 5, FIG. 5*a*. The openings for screws 9, 10 are formed with the possibility of displacement of screws in them.

The guides of the movable table through the balls 11 in the separator 12, FIG. 5*b*, 5*c*, adjoin the lateral guides 2 which are fixed on the planes of rectangular angles 3 with the possibility of their preliminary orientation in these planes by means of the screws 14. The angles are fixed with orthogonal planes in the frame 15 with the possibility of their preliminary orientation in the plane of the frame by means of the screws mounted in the openings 16, FIG. 5*c*. This arrangement of the side guides allows to perform their mounting practically completely without gaps along two planes.

For weakening of low frequency mechanical interferences which are created during a stepped mode of operation of the drive, the frame 15, FIGS. 5*b*, 5*c*, is formed as an integral rectangular cantilever with the flange 17 for fixing the drive and side reinforcing ribs 18.

For weakening of high frequency mechanical interferences which accompany the operation of the piezoelectric drive, the adjoining of the side angles 13, the drive 3, and other elements with the frame, is performed through a special steps-soles 19 formed on the setting planes of the frame, FIG. 5*c*, with the possibility of forming of inter-plane air gaps 20, FIG. 5, FIG. 5*b*. In this process, weakening of ultrasound microvibrations is performed due to reduction of the area of adjoining of the contacting surfaces.

The nut 21, FIG. 5*b*, FIG. 5*c*, is rigidly fixed on the movable table 1, FIG. 5, in the setting openings 6, FIG. 5*a*. The screw 4 adjoins the nut 21 and with its one end, through the ball 22, abuts against an immovable cantilever 23 fixed on the frame 15 through a backlash-compensating screw 24, FIGS. 5*b*, 5*c*. The screw 4 is connected by another end with the shaft of the drive 3, wherein between the precision thread of the screw 4 and the element of fixing of the screw to the shaft, a flexible connection 25 is provided in form of a few slots with formation of thin elastic plate-shaped elements with a thickness 100 . . . 400 μm, which are offset relative to one another by 90°. This arrangement provides a stabile high frequency vibro insulation of the screw 4 from the housing through the ball 22 and of the screw 4 from the shaft of the drive 3 through flexible connection 25 in a range of thicknesses of the partitions 100 . . . 200 μm with a simultaneous elimination of a backlash in the system. In this process the accuracy of the micromanipulator is increased due to compensation of harmful moments which are created during linear and angular displacements of the shaft of the drive relative to the screw 4.

The movable table by two symmetrical springs 26 that operate for stretching and are fixed with one end on the immovable cantilever 23, FIG. 5*b*, 5*c* by regulating screws 27 and fixed with another end of the table by means of a cantilever 28, is pressed through a ball 22 to immovable cantilever 23. This arrangement with the use of two springs for stretching is the most efficient damper for accompanying micromechanical interferences from the drive and simultaneously is more stabile to side moments which are created due to possible non-coaxiality during the operation of the drive, and therefore has less deviations from linearity of displacement and increased accuracy.

Since the piezoelectric drive has a sufficiently high specific moment, a wedging is not excluded in extreme positions of the movable table of the micromanipulator on the screw-nut, or a tearing off of the flexible connection 25 due to "twisting". In view of this, in a construction of the micromanipulator, a device for automatic switching off of a corresponding direction of rotation of the piezoelectric drive in extreme positions is provided. This device can be composed of two microswitches 29, FIG. 5*c*, located on the frame 15 on the axis of movement of the movable table. The triggering of the microswitches is performed by means of movable cam, fixed on the table 1 by means of setting openings 30, FIG. 5*a*, and located between the microswitches. Each microswitch is connected to a corresponding annular piezoelement so that in an initial position it commutates a circuit of excitation of the corresponding piezoelement (from the amplifier 14, FIG. 2), and breaks the circuit of excitation of the corresponding piezoelement when microswitch is triggered.

FIG. 6 shows a two-axes micromanipulator, in which additionally the identical second micromanipulator is arranged on the first micromanipulator so that their axis of displacement are perpendicular to one another. Such a micromanipulator includes a drive 1 of the first micromanipulator, a movable table 2 of the first micromanipulator, with linear guides and all other elements located on the frame 3, a drive 4 of the second micromanipulator, a movable table 5 of the second micromanipulator and a frame 6 of the second micromanipulator. The immovable table 5 of the second micromanipulator is fixed on the frame 3 of the first micromanipulator through a transitional plate 7 at an angle of 90°. Such a micromanipulator allows free maneuvering in a flat space by means of two linear axes.

FIG. 7 shows a three-axes micromanipulator, in which in addition, the identical third micromanipulator is mounted on the second micromanipulator so that all three axes of displacement are orthogonal to one another. The frame 10 of the third micromanipulator is fixed on the housing 6 of the second micromanipulator at an angle 90° by means of a rectangular cantilever 11. Such a micromanipulator allows free maneuvering in a three-dimensional space by means of three linear axis.

For the purpose of reducing a degree of penetration of high-frequency ultrasound oscillations from one coordinate to the other, all coordinates adjoin one another through special steps-soles 12 that are formed on transitional elements, movable tables and frames, with the possibility of forming interplane air gaps 13, FIG. 6, FIG. 7.

During the assembly of the micromanipulator the most "rigid" are the axes which are located closer to the point of fixing of the micromanipulator (to the clamp). The most "rigid" must be those coordinates that operate in a plane of the table of the microscope. Therefore the first micromanipulator (with the drive 1) shown in FIG. 6, FIG. 7 is arranged on the movable vertical axle 14 (for the purpose of turning in a plane of the table), which are fixed on the clamp 14 so that the axis of displacement of the first micromanipulator is directed along the longitudinal coordinate of the table, and adjoining of the micromanipulator with the axle 14 is formed through a movable table 2.

With the above described arrangement, the first coordinate becomes the most "rigid" and therefore the most inertial, since all subsequent coordinates are mounted on it. The most movable must be the longitudinal coordinate, since the main maneuvers are performed by this coordinate (for example approach to a cage, a breakthrough of membrane of a cell). Therefore the axis of displacement of the second micromanipulator with the drive 4, FIG. 6, FIG. 7, is directed along the longitudinal coordinate of the table, and its adjoining with a frame 3 of the first micromanipulator is performed through a movable table 5.

The third coordinate operates in accordance with a "height" or a focus of the microscope and becomes the least rigid. Therefore the axis, of displacement of the third micromanipulator with a drive 8, FIG. 7, is directed vertically to the plane of the table, and its fixing for the purpose of decreasing the rigidity is performed through the rectangular cantilever 11 with the side reinforcing ribs, that adjoins with the frame 6 of the second micromanipulator and the frame 10 of the third micromanipulator.

For the purpose of providing rotatable degrees of freedom of the micromanipulator, the movable table can fixedly adjoin directly the shaft of the drive, and a rotary axis is provided directly by a gapless axis of the drive, which after removing of excitation from the drive performs the function of a positioning element due to its own moment of self braking $M_{self}$ of the drive. The construction of this micromanipulator with one rotary degree of freedom is shown in FIG. 8, and with two rotary degrees of freedom is shown in FIG. 8a (shafts of the drives orthogonal to one another). The drive 2 performs a turning in the plane of a table, while the drive 4 performs a turning in a vertical plane.

For the purpose of providing operability of the micromanipulator in a flat polar system of coordinates, a construction is proposed as shown in FIG. 9. In such a micromanipulator, on the movable table 3 a second micromanipulator is installed with an offset relative to the shaft of the first drive 2, so that the shaft of the drive 4 is parallel to the shaft of the drive 2. By means of the drive 2, a turning in a plane of the table of the microscope is performed, and by means of the drive 4 a radius of this turning is changed.

For the purpose of providing a "pumping through" along the level of the micromanipulator with the flat polar system of coordinates, i.e. for operation in a cylindrical system of coordinates, additionally a third micromanipulator is arranged on the table 5 of the second micromanipulator, FIG. 9a, so that the shaft of the drive 6 is orthogonal to the shaft of the drive 4.

As shown from corresponding evaluations, the proposed micromanipulators allow to obtain the following main technical characteristics:

| | |
|---|---|
| Linear resolution | 0.001 . . . 0.0 μm. |
| Angular resolution | 0.5 angular seconds |
| Linear range of displacement | 10 . . . 100 mm |
| Angular range of displacement | 180 . . . 360 ang. degree |
| Linear ranges in of speeds | 0.01 . . . 250 μm/sec. |
| Angular ranges of speeds | 0.5 ang. sec/sec . . . 360 ang degree/sec. |
| Linear stability of positioning | 0.005 μm/hours at 20° C. |
| Angular stability of positioning | 2.5 ang sec/hour at 20° C. |
| Consumed power (in one channel) | 2 . . . 3 Wt. |

Such a micromanipulators will be widely used among scientists and experts which are involved in work related to a live cell in a microscopic field. Broad functional possibilities of such micromanipulators formed in accordance with the present invention, allow to use them widely, not only in unique medico-biological technologies, but also in various areas of science and technology.

The invention claimed is:

1. A micromanipulator containing a movable table connected with a drive that is connected to a control bock, wherein the drive is formed as a shaft with a rotor connected through pushers with annular piezoelements, one of which is mounted on the shaft, while another is mounted on a housing, characterized in that the control block of each piezoelement is formed as successively connected a generator of high frequency pulses of excitation of a piezoelement, a controlled key and an amplifier connected to a corresponding piezoelement.

2. A micromanipulator according to claim 1, characterized in that each control block of the corresponding piezoelement is additionally provided with successively arranged a block of forming frequency of pulse packets of excitation of the piezoelements and a block of forming of duration of pulse packets of excitation connected to a controlling input of the key.

3. A micromanipulator according to claim 2, characterized in that a frequency of the pulse packets of excitation is greater than 2 kHz.

4. A micromanipulator according to claim 2, characterized in that to a controlling input of the block of forming of duration of the pulse packets of excitation of the piezoelement, a joystick is connected.

5. A micromanipulator according to claim 4, characterized in that a duration of the packets of pulses of excitation at an output of the block of forming of duration is proportional to a deviation of a handle of the joystick.

6. A micromanipulator according to claim 4, characterized in that a duration of the packet of pulses of excitation at an output of the block of forming of duration is proportional to an logarithm of deviation of a handle of the joystick.

7. A micromanipulator according to claim 2, characterized in that one of the outputs of a generator of high frequency pulses of excitation of the piezoelement is connected to an input of the block of forming of frequency of packets of pulses of excitation of the piezoelement.

8. A micromanipulator according to claim 1, characterized in that the control block of the piezoelement is provided with a block of forming of a single packet of pulses of excitation of the piezoelement, connected to a controlling input of the key.

9. A micromanipulator according to claim 1, characterized in that the annular piezoelements are formed as ring-shaped resonators with a radial shape of oscillations, whose external cylindrical surface is surrounded by a wave casing, on which pushers are mounted and abut against an inner surface of the rotor.

10. A micromanipulator according to claim 9, characterized in that the annular piezoelements are polarized along a normal to their flat end surfaces, electrodes are applied to the flat end surface, and their parameters satisfy the ratio D/d~2, d/2~h, where D—an outer diameter of the annular piezoelement, d—an inner diameter of the annular piezoelement, h—a height of the ring-shaped piezoelement.

11. A micromanipulator according to claim 1, characterized in that the frequency of the generator of high frequency pulses of excitation of the piezoelements correspond to a zero mode of radial oscillations of the ring-shaped resonator.

12. A micromanipulator according to claim 9, characterized in that the wave casing is formed as a thin-walled cylinder with fields which are turned at both sides and form ring-shaped reinforcing ribs, wherein the said reinforcing ribs are cut by slots, in which the pushers are fixed with one end and formed as thin plates.

13. A micromanipulator according to claim 12, characterized in that the pushers in the wave casing are arranged at an angle to a radial direction.

14. A micromanipulator according to claim 12, characterized in that on the pushers, casings of sound-insulating material are mounted and adjoin with the pushers along side end surfaces.

15. A micromanipulator according to claim 1, characterized in that the rotor is formed as two thin-walled cylinders arranged on an axial system.

16. A micromanipulator according to claim 15, characterized in that the axial system is formed as a cylindrical sliding bearing of a sound insulating material with a central flange, on which the thin-walled cylinders are fixed.

17. A micromanipulator according to claim 1, characterized in that a connection of the second piezoelement, mounted on a housing, is formed as a rubber ring mounted in a threaded fixing slot in the housing of the drive, a fluoroplastic ring mounted in a threaded fixing slot in a pressing flange, and elements for fixing the pressing flange to the housing of the drive.

18. A micromanipulator according to claim 1, characterized in that connections of the first piezoelement arranged on the shaft of the drive is formed as a rubber ring arranged in a threaded fixing slot on an axial flange rigidly connected with the shaft, a fluoroplastic ring mounted in a threaded fixing slot in a pressing flange, and elements for fixing the pressing flange to an axial flange which is rigidly connected to the shaft.

19. A micromanipulator according to claim 1, characterized in that the housing of the drive is formed as a rigid square flange with cylindrical grooves and additionally is provided with a casing, wherein the casing is formed as a cylinder that ends in an analogous square flange, which are rigidly connected with one another.

20. A micromanipulator according to claim 19, characterized in that the shaft is mounted in ball bearings, one of which is mounted in a housing, and another mounted in a casing, wherein a working part of the shaft extends outwardly beyond the housing.

21. A micromanipulator according to claim 1, characterized in that a movable table is arranged in composite linear guides and connected with the drive through a screw-nut, wherein a micrometric nut is fixedly mounted on the movable table.

22. A micromanipulator according to claim 21, characterized in that the movable table is formed as a working surface with setting spots, with an opposite side provided with setting openings for the micrometric nut and an integral longitudinal cantilever with a setting surface perpendicular to a working surface of the table and parallel to an axis of a setting opening for the micrometric nut, and with another side provided with an analogous cantilever with a possibility of its preliminary orientation in a plane parallel to the plane of the table, wherein guides are mounted on both setting planes of each cantilever with a possibility of the preliminary orientation on setting planes perpendicular to the plane of the table.

23. A micromanipulator according to claim 22, characterized in that the guides of the movable table adjoin through balls or rollers with side guides, which are fixed on planes of rectangular angles with a possibility of their preliminary orientation in these planes, and angles are fixed by orthogonal planes on a frame with a possibility of their preliminary orientation in a plane of the frame.

24. A micromanipulator according to claim 23, characterized in that the frame is formed as an integral rectangular cantilever with a flange for fixing a drive and side reinforcing ribs.

25. A micromanipulator according to claim 24, characterized in that the adjoining of the side angles, drive and other elements with the frame is performed through special step-soles formed on the setting planes of the frame, with a possibility of forming of inter-plane air gaps.

26. A micromanipulator according to claim 21, characterized that a screw adjoins a micrometric nut and abuts with one end through a ball against an immovable cantilever fixed on the frame, and with another end is connected to the shaft of the drive, wherein between a thread and an element of fixing of the screw to the shaft an elastic connection is formed by a few slots with forming of thin flexible plate-like elements with a thickness 100 . . . 400 μm which are offset relative to one another by 90°.

27. A micromanipulator according to claim 21, characterized in that the movable table with two symmetrical springs operating for stretching and connected with one end to the immovable lever and with another end to the movable table, is pressed through a ball to an immovable cantilever.

28. A micromanipulator according to claim 1, characterized in that it is provided with a device for automatic switching off of a corresponding direction of rotation of the piezoelectric drive in extreme positions.

29. A micromanipulator according to claim 28, characterized in that the device for automatic switching off is formed as two microswitches, located on a frame along an axis of displacement of a cam fixed on the movable table, wherein each microswitch is connected to a corresponding annular piezoelement so that in an initial position it commutates a circuit of excitation of the corresponding piezoelement and opens a circuit of excitation of a corresponding piezoelement during triggering of the microswitch.

30. A micromanipulator according to claim 21, characterized in that additionally an identical second micromanipulator is mounted on the first micromanipulator so that the axes of displacement of the movable tables are perpendicular to one another.

31. A micromanipulator according to claim 30, characterized in that additionally, an identical third manipulator is arranged on the second micromanipulator so that all three axes of displacement of movable tables are orthogonal.

32. A micromanipulator according to claim 30, characterized in that all micromanipulators adjoin one another through special steps-soles formed on transitional elements, movable tables and frames, with a possibility of forming of inter-plane air gaps.

33. A micromanipulator according to claim 1, characterized in that it is arranged on a movable vertical axle which is fixed on a clamp, so that its axis of displacement is directed along a transverse coordinate of a working table, and adjoinment of the micromanipulator with the axle is performed through a movable table.

34. A micromanipulator according to claim 30, characterized in that the axis of displacement of the second micromanipulator is directed along a longitudinal coordinate of the working table, and its adjoining with the frame of the first micromanipulator is formed through a movable table.

35. A micromanipulator according to claim 31, characterized in that the axis of displacement of the third micromanipulator is directed vertically to a plane of a working table, and its fixation is formed through a rectangular cantilever with side reinforcing ribs, which adjoins the frame of the second micromanipulator and the frame of the third micromanipulator.

36. A micromanipulator according to claim 1, characterized in that the movable table rigidly adjoins the shaft of the drive.

37. A micromanipulator according to claim 36, characterized in that the second identical manipulator is arranged on the movable table, and the shafts of the drives are perpendicular to one another.

38. A micromanipulator according to claim 36, characterized in that on the movable table, a second micromanipulator is installed with an offset relative to the shaft so that the shafts of the drives are parallel to one another.

39. A micromanipulator according to claim 38, characterized in that on the movable table of the second micromanipulator, a third micromanipulator is installed so that the shaft of the third micromanipulator is perpendicular to the shaft of the second micromanipulator.

* * * * *